(12) United States Patent
Gall et al.

(10) Patent No.: US 9,910,047 B2
(45) Date of Patent: Mar. 6, 2018

(54) BIOMARKERS RELATED TO INSULIN RESISTANCE PROGRESSION AND METHODS USING THE SAME

(71) Applicant: Metabolon, Inc., Durham, NC (US)

(72) Inventors: Walter Gall, Chapel Hill, NC (US); Jeffery Edmond Cobb, Chapel Hill, NC (US); Kirk Lane Pappan, Rougemont, NC (US)

(73) Assignee: Metabolon, Inc., Morrisville, NC (US)

( * ) Notice: Subject to any disclaimer, the term of this patent is extended or adjusted under 35 U.S.C. 154(b) by 0 days.

(21) Appl. No.: 14/763,962

(22) PCT Filed: Jan. 16, 2014

(86) PCT No.: PCT/US2014/011759
§ 371 (c)(1),
(2) Date: Jul. 28, 2015

(87) PCT Pub. No.: WO2014/120449
PCT Pub. Date: Aug. 7, 2014

(65) Prior Publication Data
US 2015/0362510 A1 Dec. 17, 2015

Related U.S. Application Data

(60) Provisional application No. 61/758,924, filed on Jan. 31, 2013.

(51) Int. Cl.
*G01N 33/53* (2006.01)
*G01N 33/68* (2006.01)
*G06F 19/00* (2018.01)

(52) U.S. Cl.
CPC ..... *G01N 33/6893* (2013.01); *G01N 33/5308* (2013.01); *G06F 19/3431* (2013.01); *G01N 2333/46* (2013.01); *G01N 2800/042* (2013.01); *G01N 2800/32* (2013.01); *G01N 2800/324* (2013.01); *G01N 2800/50* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | |
|---|---|---|
| 2009/0012716 A1 | 1/2009 | Urdea et al. |
| 2010/0120629 A1 | 5/2010 | Ellis et al. |
| 2011/0097807 A1 | 4/2011 | Monte et al. |
| 2011/0311650 A1 | 12/2011 | Wang et al. |
| 2012/0122981 A1 | 5/2012 | Hu et al. |
| 2012/0208215 A1 | 8/2012 | Hu et al. |
| 2012/0328594 A1 | 12/2012 | McKenna et al. |
| 2014/0303228 A1* | 10/2014 | Lawton ............... G01N 33/6896 514/419 |
| 2014/0343865 A1* | 11/2014 | Brown ............... G01N 33/5011 702/19 |

OTHER PUBLICATIONS

Ganti et al. (Cancer Research 2012 vol. 72, p. 3471-3479).*
International Search Report, dated Mar. 21, 2014, for PCT/US2014/011759, filed Jan. 16, 2014.
International Preliminary Report on Patentability, dated Aug. 4, 2015, for PCT/US2014/011759, filed Jan. 16, 2014.
Supplementary European Search Report, dated May 31, 2016, for European Patent Application No. 14746017.4 filed Jul. 8, 2015.
Zhao et al., "Metabonomic fingerprints of fasting plasma and spot urine reveal human pre-diabetic metabolic traits", Metabolomics, Mar. 7, 2010, vol. 6, No. 3, pp. 362-374.
C. Herder et al., "Biomarkers for the Prediction of Type 2 Diabetes and Cardiovascular Disease", Clinical Pharmacology & Therapeutics, Jun. 8, 2011, vol. 90, No. 1, pp. 52-66.
Kaur et al.,"Quantitative metabolomic and lipidomic profiling reveals aberrant amino acid metabolism in type 2 diabetes", Molecular Biosystems, Jan. 1, 2013, vol. 9, No. 2, pp. 307-317.
Wang-Sattler et al., "Novel biomarkers for pre-diabetes identified by metabolomics", Molecular Systems Biology, Sep. 25, 2012, vol. 8, pp. 1-11.
B. Buijsse et al., "Risk Assessment Tools for Identifying Individuals at Risk of Developing Type 2 Diabetes", Epidemiologic Reviews, May 27, 2011, vol. 33, No. 1, pp. 46-62.

* cited by examiner

*Primary Examiner* — Changhwa J Cheu
(74) *Attorney, Agent, or Firm* — Brinks Gilson & Lione

(57) ABSTRACT

Biomarkers relating to insulin resistance and insulin resistance-related disorders are provided, as well as methods for using such biomarkers as biomarkers for insulin resistance, dysglycemia, type-2 diabetes, and cardiovascular disease. In addition, methods for monitoring the respective disorders or conditions of a subject are also provided. Also provided are suites of small molecule entities as biomarkers for insulin resistance, dysglycemia, type-2 diabetes, and cardiovascular disease.

22 Claims, No Drawings

BIOMARKERS RELATED TO INSULIN RESISTANCE PROGRESSION AND METHODS USING THE SAME

CROSS-REFERENCE TO RELATED APPLICATIONS

This application is a National Stage application of International Application No. PCT/US2014/011759, filed Jan. 16, 2014, which claims the benefit of U.S. Provisional Patent Application No. 61/758,924, filed Jan. 31, 2013, the entire contents of which are hereby incorporated herein by reference.

FIELD

The invention generally relates to biomarkers for prediction of the progression of insulin resistance and susceptibility to and development of type 2 diabetes and cardiovascular disease in pre-diabetic individuals, methods for identifying biomarkers predictive of progression of insulin resistance, type 2 diabetes and cardiovascular disease and/or insulin resistance and insulin resistance-related disorders and methods based on the same biomarkers.

BACKGROUND

Diabetes is classified as either type 1 (early onset) or type 2 (adult onset), with type 2 comprising 90-95% of the cases of diabetes. Diabetes is the final stage in a disease process that begins to affect individuals long before the diagnosis of diabetes is made. Type 2 diabetes develops over 10 to 20 years and results from an impaired ability to utilize glucose (glucose utilization, glucose uptake in peripheral tissues) due to impaired sensitivity to insulin (insulin resistance).

Moreover, insulin resistance is central to development of a number of different diseases and conditions, such as cardiovascular disease, metabolic syndrome, nonalcoholic steatohepatitis (NASH), polycystic ovary syndrome (PCOS), and hypertension.

In pre-diabetes, insulin becomes less effective at helping tissues metabolize glucose. Pre-diabetics may be detectable as early as 20 years before diabetic symptoms become evident. Studies have shown that although patients show very few overt symptoms, long-term physiological damage is already occurring at this stage. Up to 60% of these individuals will progress to type 2 diabetes within 10 years.

The American Diabetes Association (ADA) has recommended routine screening to detect patients with pre-diabetes. Current screening methods for pre-diabetes include the fasting plasma glucose (FPG) test, the oral glucose tolerance test (OGTT), the fasting insulin test and the hyperinsulinemic euglycemic clamp (HI clamp). The first two tests are used clinically whereas the latter two tests are used extensively in research but rarely in the clinic. In addition, mathematical means (e.g., HOMA, QUICKI) that consider the fasting glucose and insulin levels together have been proposed. However, normal plasma insulin concentrations vary considerably between individuals as well as within an individual throughout the day. Further, these methods suffer from variability and methodological differences between laboratories and do not correlate rigorously with HI clamp studies.

Worldwide, an estimated 194 million adults have type 2 diabetes and this number is expected to increase to 333 million by 2025, largely due to the epidemic of obesity in westernized societies. In the United States, it is estimated that over 54 million adults are pre-diabetic. There are approximately 1.5 million new cases of type 2 diabetes a year in the United States. The annual US healthcare cost for diabetes is estimated at $174 billion. This figure has risen more than 32% since 2002. In industrialized countries such as the U.S., about 25% of medical expenditures treat glycemic control, 50% is associated with general medical care associated with diabetes, and the remaining 25% of the costs go to treat long-term complications, primarily cardiovascular disease. Considering the distribution of the healthcare costs and the fact that insulin resistance is a direct causal factor in cardiovascular disease and diabetes progression, it is no surprise that cardiovascular disease accounts for 70-80% of the mortality observed for diabetic patients. Detecting and preventing type 2 diabetes has become a major health care priority.

Diabetes may also lead to the development of other diseases or conditions, or is a risk factor in the development of conditions such as Metabolic Syndrome and cardiovascular diseases. Metabolic Syndrome is the clustering of a set of risk factors in an individual. According to the American Heart Association these risk factors include: abdominal obesity, decreased ability to properly process glucose (insulin resistance or glucose intolerance), dyslipidemia (high triglycerides, high LDL, low HDL cholesterol), hypertension, prothrombotic state (high fibrinogen or plasminogen activator inhibitor-1 in the blood) and proinflammatory state (elevated C-reactive protein in the blood). Metabolic Syndrome is also known as syndrome X, insulin resistance syndrome, obesity syndrome, dysmetabolic syndrome and Reaven's syndrome. Patients diagnosed with Metabolic Syndrome are at an increased risk of developing diabetes, cardiac and vascular disease. It is estimated that, in the United States, 20% of the adults (>50 million people) have metabolic syndrome. While it can affect anyone at any age, the incidence increases with increasing age and in individuals who are inactive, and significantly overweight, especially with excess abdominal fat.

Type 2 diabetes is the most common form of diabetes in the United States. According to the American Diabetes Foundation over 90% of the US diabetics suffer from Type 2 diabetes. Individuals with Type 2 diabetes have a combination of increased insulin resistance and decreased insulin secretion that combine to cause hyperglycemia. Most persons with Type 2 diabetes have Metabolic Syndrome.

The diagnosis for Metabolic Syndrome is based upon the clustering of three or more of the risk factors in an individual. A variety of medical organizations have definitions for the Metabolic Syndrome. The criteria proposed by the National Cholesterol Education Program (NCEP) Adult Treatment Panel III (ATP III), with minor modifications, are currently recommended and widely used in the United States.

The American Heart Association and the National Heart, Lung, and Blood Institute recommend that the metabolic syndrome be identified as the presence of three or more of these components: increased waist circumference (Men—equal to or greater than 40 inches (102 cm), Women—equal to or greater than 35 inches (88 cm); elevated triglycerides (equal to or greater than 150 mg/dL); reduced HDL ("good") cholesterol (Men—less than 40 mg/dL, Women—less than 50 mg/dL); elevated blood pressure (equal to or greater than 130/85 mm Hg); elevated fasting glucose (equal to or greater than 100 mg/dL).

Type 2 diabetes develops slowly and often people first learn they have type 2 diabetes through blood tests done for another condition or as part of a routine exam. In some cases, type 2 diabetes may not be detected before damage to eyes, kidneys or other organs has occurred. A need exists for an objective, biochemical evaluation (e.g. lab test) that can be administered by a primary care provider to identify individuals that are at risk of developing Metabolic Syndrome or Type 2 diabetes.

Newer, more innovative molecular diagnostics that reflect the mechanisms of the patho-physiological progression to pre-diabetes and diabetes are needed because the prevalence of pre-diabetes and diabetes is increasing in global epidemic proportions. Mirroring the obesity epidemic, pre-diabetes and diabetes are largely preventable but are frequently undiagnosed or diagnosed too late due to the asymptomatic nature of the progression to clinical disease.

Although insulin resistance plays a central role in the development of numerous diseases, it is not readily detectable using many of the clinical measurements for pre-diabetic conditions. Insulin resistance develops prior to the onset of hyperglycemia and is associated with increased production of insulin. Over time (decades) the ability of the cell to respond to insulin decreases and the subject becomes resistant to the action of insulin (i.e., insulin resistant, IR). Eventually the beta-cells of the pancreas cannot produce sufficient insulin to compensate for the decreased insulin sensitivity and the beta-cells begin to lose function and apoptosis is triggered. Beta-cell function may be decreased as much as 80% in pre-diabetic subjects. As beta-cell dysfunction increases the production of insulin decreases resulting in lower insulin levels and high glucose levels in diabetic subjects. Vascular damage is associated with the increase in insulin resistance and the development of type 2 diabetes.

Therefore there is an unmet need for diagnostic biomarkers and tests that can determine the risk of developing insulin resistance, type 2 diabetes, and cardiovascular disease in subjects within at least 3 years to at least 5 years and for progression of insulin resistance to type 2 diabetes and/or cardiovascular disease in non-diabetic subjects with insulin resistance. Insulin resistance biomarkers and diagnostic tests can better identify and determine the risk of cardiovascular disease and/or diabetes development in an at risk subject and/or a pre-diabetic subject, can monitor disease development and progression and/or regression, can allow new therapeutic treatments to be developed and can be used to test therapeutic agents for efficacy on reversing insulin resistance and/or preventing insulin resistance and related diseases. Further, a need exists for diagnostic biomarkers to more effectively assess the efficacy and safety of pre-diabetic and diabetic therapeutic candidates.

DETAILED DESCRIPTION

The present invention relates to biomarkers predictive of an individual's risk to develop insulin resistance, dysglycemia, type-2 diabetes, and cardiovascular disease; methods of determining predisposition to insulin resistance, dysglycemia, type-2 diabetes, and cardiovascular disease; methods of monitoring progression/regression of dysglycemia, type-2 diabetes, and cardiovascular disease; methods of assessing efficacy of treatments and compositions for treating insulin resistance, dysglycemia, type-2 diabetes, and cardiovascular disease; methods of screening compositions for activity in modulating biomarkers of insulin resistance, dysglycemia, type-2 diabetes, and cardiovascular disease; methods of treating insulin resistance, dysglycemia, type-2 diabetes, and cardiovascular disease; methods of identifying subjects for treatment with insulin resistant, dysglycemia, type-2 diabetes, and cardiovascular disease therapies; methods of identifying subjects for inclusion in clinical trials of insulin resistance, dysglycemia, type-2 diabetes, and cardiovascular disease therapies; as well as other methods based on biomarkers of insulin resistance, dysglycemia, type-2 diabetes, and cardiovascular disease.

Current blood tests for insulin resistance, dysglycemia, type-2 diabetes, and cardiovascular disease perform poorly for early detection of insulin resistance, dysglycemia, type-2 diabetes, and cardiovascular disease or involve significant medical procedures.

In one embodiment, groups (also referred to as "panels") of metabolites that can be used in a simple blood, urine, etc. test to predict insulin resistance, dysglycemia, type-2 diabetes, and cardiovascular disease are identified using metabolomic analysis. Independent studies were carried out to identify a set of biomarkers that when used with a polynomic algorithm enables the early detection of changes in insulin sensitivity, dysglycemia, type-2 diabetes, and/or cardiovascular disease in a subject. The biomarkers of the instant disclosure can be used to provide a score indicating the probability of insulin resistance, dysglycemia, type-2 diabetes, and/or cardiovascular disease in a subject (e.g., "Risk Score"). The score can be based upon a clinically significant changed reference level for a biomarker and/or combination of biomarkers. The reference level can be derived from an algorithm or computed from indices for impaired glucose tolerance and can be presented in a report. The Risk Score places the subject in the risk range of insulin resistance, dysglycemia, type-2 diabetes, and/or cardiovascular disease from normal (low risk) to high risk and/or can be used to determine a probability that the subject has insulin resistance, dysglycemia, type-2 diabetes, or cardiovascular disease. Disease progression or remission can be monitored by periodic determination and monitoring of the Risk Score. Response to therapeutic intervention can be determined by monitoring the Risk Score. The Risk Score can also be used to evaluate drug efficacy or to identify subjects to be treated with insulin resistance, dysglycemia, type-2 diabetes, and/or cardiovascular disease therapies, such as insulin sensitizers, or to identify subjects for inclusion in clinical trials.

Prior to describing this invention in further detail, however, the following terms will first be defined.

Definitions

"Biomarker" means a compound, preferably a metabolite, that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test). Alternatively, the biomarkers demonstrate a correlation with insulin resistance, or particular levels or stages of insulin resistance. The range of possible correlations is between negative (−) 1 and positive (+) 1. A result of negative (−) 1 means a perfect negative correlation and a positive (+) 1 means a perfect positive correlation, and 0 means no correlation at all. A "substantial positive correlation" refers to a biomarker having a correlation from +0.25 to +1.0 with a disorder or with a clinical measurement (e.g., Rd), while a "substantial negative correlation" refers to a correlation from −0.25 to −1.0 with a given disorder or clinical measurement. A "significant positive correlation" refers to a biomarker having a correlation of from +0.5 to +1.0 with a given disorder or clinical measurement (e.g., Rd), while a "significant negative correlation" refers to a correlation to a disorder of from −0.5 to −1.0 with a given disorder or clinical measurement.

The "level" of one or more biomarkers means the absolute or relative amount or concentration of the biomarker in the sample.

"Sample" or "biological sample" or "specimen" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, adipose tissue, aortic tissue, liver tissue, blood, blood plasma, saliva, serum, cerebrospinal fluid, cystic fluid, exudates, or urine.

"Subject" means any animal, but is preferably a mammal, such as, for example, a human, monkey, non-human primate, rat, mouse, cow, dog, cat, pig, horse, or rabbit.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, an "insulin resistance-positive reference level" of a biomarker means a level of a biomarker that is indicative of a positive diagnosis of insulin resistance in a subject, and an "insulin resistance-negative reference level" of a biomarker means a level of a biomarker that is indicative of a negative diagnosis of insulin resistance in a subject. As another example, an "insulin resistance-progression-positive reference level" of a biomarker means a level of a biomarker that is indicative of progression of insulin resistance in a subject, and an "insulin resistance-regression-positive reference level" of a biomarker means a level of a biomarker that is indicative of regression of insulin resistance. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. A "reference level" may also be a "standard curve reference level" based on the levels of one or more biomarkers determined from a population and plotted on appropriate axes to produce a reference curve (e.g. a standard probability curve). Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). A standard curve reference level may be determined from a group of reference levels from a group of subjects having a particular disease state, phenotype, or lack thereof (e.g. known glucose disposal rates) using statistical analysis, such as univariate or multivariate regression analysis, logistic regression analysis, linear regression analysis, and the like of the levels of such biomarkers in samples from the group. Such reference levels may also be tailored to specific techniques that are used to measure levels of biomarkers in biological samples (e.g., LC-MS, GC-MS, etc.), where the levels of biomarkers may differ based on the specific technique that is used.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolite", or "small molecule", means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates which can be metabolized further or used to generate large molecules, called macromolecules. The term "small molecules" includes signaling molecules and intermediates in the chemical reactions that transform energy derived from food into usable forms. Examples of small molecules include sugars, fatty acids, amino acids, nucleotides, intermediates formed during cellular processes, and other small molecules found within the cell.

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

"Metabolome" means all of the small molecules present in a given organism.

"Diabetes" refers to a group of metabolic diseases characterized by high blood sugar (glucose) levels which result from defects in insulin secretion or action, or both.

"Type 2 diabetes" or "T2D" refers to one of the two major types of diabetes, the type in which the beta cells of the pancreas produce insulin, at least in the early stages of the disease, but the body is unable to use it effectively because the cells of the body are resistant to the action of insulin. In later stages of the disease the beta cells may stop producing insulin. Type 2 diabetes is also known as insulin-resistant diabetes, non-insulin dependent diabetes and adult-onset diabetes.

"Pre-diabetes" refers to one or more early diabetes-related conditions including impaired glucose utilization, abnormal or impaired fasting glucose levels, impaired glucose tolerance, impaired insulin sensitivity and insulin resistance.

"Insulin resistant" refers to the condition when cells become resistant to the effects of insulin—a hormone that regulates the uptake of glucose into cells—or when the amount of insulin produced is insufficient to maintain a normal glucose level. Cells are diminished in the ability to respond to the action of insulin in promoting the transport of the sugar glucose from blood into muscles and other tissues (i.e. sensitivity to insulin decreases). Eventually, the pancreas produces far more insulin than normal and the cells continue to be resistant. As long as enough insulin is produced to overcome this resistance, blood glucose levels remain normal. Once the pancreas is no longer able to keep up, blood glucose starts to rise, resulting in diabetes. Insulin resistance ranges from normal (insulin sensitive) to insulin resistant (IR).

"Insulin sensitivity" refers to the ability of cells to respond to the effects of insulin to regulate the uptake and utilization of glucose. Insulin sensitivity ranges from normal (insulin sensitive) to Insulin Resistant (IR).

The "Risk Score" or "Disease Risk (DR) Score" is a measure of the probability of insulin resistance, dysglycemia, type-2 diabetes, and/or cardiovascular disease in a subject. As used herein, the term Disease Risk Score or DR Score is used generically to exemplify the invention and may refer to risk of any of the diseases associated with insulin resistance and pre-diabetes while a specific Risk Score refers to that specific disease. For example, an "IR Risk Score" is based upon the predicted glucose disposal rate calculated using the insulin resistance biomarkers (e.g. along with models and/or algorithms) that will allow a physician to determine the probability that a subject is insulin resistant. Risk Scores for determining the probability that a subject is dysglycemic (e.g., "Dysglycemia Risk Score"), type-2 diabetic (e.g., "T2D Risk Score"), and/or has cardiovascular disease (e.g., "CVD Risk Score") are based upon measuring the levels of biomarkers for dysglycemia, type-2 diabetes or cardiovascular disease and using said measurements in a mathematical model (e.g. statistical model, algorithm).

"Glucose utilization" refers to the absorption of glucose from the blood by muscle and fat cells and utilization of the sugar for cellular metabolism. The uptake of glucose into cells is stimulated by insulin.

"Rd" refers to glucose disposal rate (Rate of disappearance of glucose), a metric for glucose utilization. The rate at which glucose disappears from the blood (disposal rate) is an indication of the ability of the body to respond to insulin (i.e. insulin sensitive). There are several methods to determine Rd and the hyperinsulinemic euglycemic clamp is regarded as the "gold standard" method. In this technique, while a fixed amount of insulin is infused, the blood glucose is "clamped" at a predetermined level by the titration of a variable rate of glucose infusion. The underlying principle is that upon reaching steady state, by definition, glucose disposal is equivalent to glucose appearance. During hyperinsulinemia, glucose disposal (Rd) is primarily accounted for by glucose uptake into skeletal muscle, and glucose appearance is equal to the sum of the exogenous glucose infusion rate plus the rate of hepatic glucose output (HGO). The rate of glucose infusion during the last 30 minutes of the test determines insulin sensitivity. If high levels of glucose (Rd=7.5 mg/kg/min or higher) are required, the patient is insulin-sensitive. Very low levels (Rd=4.0 mg/kg/min or lower) of required glucose indicate that the body is resistant to insulin action. Levels between 4.0 and 7.5 mg/kg/min (Rd values between 4.0 mg/kg/min and 7.5 mg/kg/min) of required glucose are not definitive and suggest sensitivity to insulin is impaired and that the subject may have "impaired glucose tolerance," which may sometimes be a sign of insulin resistance.

"Mffm" and "Mwbm" refer to glucose disposal (M) calculated as the mean rate of glucose infusion during the past 60 minutes of the clamp examination (steady state) and expressed as milligrams per minute per kilogram of fat free mass (ffm) or whole body mass (wbm). Subjects with an Mffm less than 45 umol/min/kg ffm are generally regarded as insulin resistant. Subjects with an Mwbm of less than 5.6 mg/kg/min are generally regarded as insulin resistant.

"Impaired fasting glucose (IFG)" and "impaired glucose tolerance (IGT)" are the two clinical definitions of "pre-diabetes". IFG is defined as a fasting blood glucose concentration of 100-125 mg/dL. IGT is defined as a postprandial (after eating) blood glucose concentration of 140-199 mg/dL. It is known that IFG and IGT do not always detect the same pre-diabetic populations. Between the two populations there is approximately a 60% overlap observed. Fasting plasma glucose levels are a more efficient means of inferring a patient's pancreatic function, or insulin secretion, whereas postprandial glucose levels are more frequently associated with inferring levels of insulin sensitivity or resistance. IGT is known to identify a greater percentage of the pre-diabetic population compared to IFG. The IFG condition is associated with lower insulin secretion, whereas the IGT condition is known to be strongly associated with insulin resistance. Numerous studies have been carried out that demonstrate that IGT individuals with normal FPG values are at increased risk for cardiovascular disease. Patients with normal FPG values may have abnormal postprandial glucose values and are often unaware of their risk for pre-diabetes, diabetes, and cardiovascular disease.

"Fasting plasma glucose (FPG) test" is a simple test measuring blood glucose levels after an 8 hour fast. According to the ADA, blood glucose concentration of 100-125 mg/dL is considered IFG and defines pre-diabetes whereas ≥126 mg/dL defines diabetes. As stated by the ADA, FPG is the preferred test to diagnose diabetes and pre-diabetes due to its ease of use, patient acceptability, lower cost, and relative reproducibility. The weakness in the FPG test is that patients are quite advanced toward Type 2 Diabetes before fasting glucose levels change.

"Oral glucose tolerance test (OGTT)", a dynamic measurement of glucose, is a postprandial measurement of a patient's blood glucose levels after oral ingestion of a 75 g glucose drink. Traditional measurements include a fasting blood sample at the beginning of the test, a one hour time point blood sample, and a 2 hour time point blood sample. A patient's blood glucose concentration at the 2 hour time point defines the level of glucose tolerance: Normal glucose tolerance (NGT)≤140 mg/dL blood glucose; Impaired glucose tolerance (IGT)=140-199 mg/dL blood glucose; Diabetes ≥200 mg/dL blood glucose. As stated by the ADA, even though the OGTT is known to be more sensitive and specific at diagnosing pre-diabetes and diabetes, it is not recommended for routine clinical use because of its poor reproducibility and difficulty to perform in practice.

"Fasting insulin test" measures the circulating mature form of insulin in plasma. The current definition of hyperinsulinemia is difficult due to lack of standardization of insulin immunoassays, cross-reactivity to proinsulin forms, and no consensus on analytical requirements for the assays. Within-assay CVs range from 3.7%-39% and among-assay CVs range from 12%-66%. Therefore, fasting insulin is not commonly measured in the clinical setting and is limited to the research setting.

The "hyperinsulinemic euglycemic clamp (HI clamp)" is considered worldwide as the "gold standard" for measuring insulin resistance in patients. It is performed in a research setting, requires insertion of two catheters into the patient and the patient must remain immobilized for up to six hours. The HI clamp involves creating steady-state hyperinsulinemia by insulin infusion, along with parallel glucose infusion in order to quantify the required amount of glucose to maintain euglycemia (normal concentration of glucose in the blood; also called normoglycemia). The result is a measure of the insulin-dependent glucose disposal rate (Rd), measuring the peripheral uptake of glucose by the muscle (primarily) and adipose tissues. This rate of glucose uptake is notated by M, whole body glucose metabolism by insulin action under steady state conditions. Therefore, a high M indicates high insulin sensitivity and a lower M value indicates reduced insulin sensitivity, i.e. insulin resistant. The HI clamp requires three trained professionals to carry out the procedure, including simultaneous infusions of insulin and glucose over 2-4 hours and frequent blood sampling every 5 minutes for analysis of insulin and glucose levels. Due to the high cost, complexity, and time required for the HI clamp, this procedure is strictly limited to the clinical research setting.

"Obesity" refers to a chronic condition defined by an excess amount body fat. The normal amount of body fat (expressed as percentage of body weight) is between 25-30% in women and 18-23% in men. Women with over 30% body fat and men with over 25% body fat are considered obese.

"Body Mass Index, (or BMI)" refers to a calculation that uses the height and weight of an individual to estimate the amount of the individual's body fat. Too much body fat (e.g. obesity) can lead to illnesses and other health problems. BMI is the measurement of choice for many physicians and researchers studying obesity. BMI is calculated using a mathematical formula that takes into account both height and weight of the individual. BMI equals a person's weight in kilograms divided by height in meters squared. (BMI=kg/m$^2$). Subjects having a BMI less than 19 are considered to be underweight, while those with a BMI of between 19 and 25 are considered to be of normal weight, while a BMI of between 25 to 29 are generally considered overweight, while individuals with a BMI of 30 or more are typically considered obese. Morbid obesity refers to a subject having a BMI of 40 or greater.

"Insulin resistance-related disorder" refers to diseases or disorders associated with insulin resistance and includes dysglycemia, type-2 diabetes, cardiovascular disease (including myocardial infarction, stroke).

I. Biomarkers

The biomarkers described herein were discovered using metabolomic profiling techniques. Such metabolomic profiling techniques are described in more detail in the Examples set forth below as well as in U.S. Pat. Nos. 7,005,255 and 7,329,489 and U.S. Pat. No. 7,635,556, U.S. Pat. No. 7,682,783, U.S. Pat. No. 7,682,784, and U.S. Pat. No. 7,550,258, the entire contents of all of which are hereby incorporated herein by reference.

Generally, metabolic profiles may be determined for biological samples from human subjects diagnosed with a condition such as being insulin resistant as well as from one or more other groups of human subjects (e.g., healthy control subjects with normal glucose tolerance, subjects with impaired glucose tolerance, subjects with insulin resistance, or having known glucose disposal rates, subjects with type 2 diabetes, subjects having cardiovascular disease (e.g., subjects having suffered myocardial infarction or stroke), human subjects that develop type-2 diabetes within a time frame (e.g. those who develop type-2 diabetes within 3 years, those subjects who develop type-2 diabetes within 5 years), human subjects who do not develop type-2 diabetes, or human subjects that do not develop cardiovascular disease). The metabolic profile for biological samples from one group of subjects may then be compared to the metabolic profile for biological samples from the one or more other groups of subjects. The comparisons may be conducted using models or algorithms, such as those described herein. Those molecules differentially present, including those molecules differentially present at a level that is statistically significant, in the metabolic profile of samples from subjects of one group as compared to another group (e.g., insulin sensitive subjects that develop type 2 diabetes vs. insulin sensitive subjects that do not develop type 2 diabetes, insulin sensitive subjects that develop cardiovascular disease vs. insulin sensitive subjects that do not develop cardiovascular disease) may be identified as biomarkers to distinguish those groups.

Biomarkers for use in the methods disclosed herein may be obtained from any source of biomarkers related to insulin resistance, dysglycemia, type-2 diabetes, and/or cardiovascular disease. Biomarkers for use in methods disclosed herein relating to predicting development of insulin resistance include 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine and subsets thereof. Additional biomarkers for use in combination with those disclosed herein include those disclosed in International Patent Application Publication No. WO 2009/014639 and U.S. application Ser. No. 12/218,980, filed Jul. 17, 2008, the entireties of which are hereby incorporated by reference herein. In one aspect, the biomarkers correlate to insulin resistance.

Biomarkers for use in methods disclosed herein relating to predicting development of type 2 diabetes include those markers listed in Table 1 and Table 2 and subsets thereof. In one embodiment the biomarkers include 3-phenylpropionate (hydrocinnamate), 3-(4-hydroxyphenyl)lactate, indolelactate, 5-oxoproline, bradykinin-hydroxy-pro, mannose, 7-alpha-hydroxy-3-oxo-4-cholestenoate (7-Hoca), heme, glycerol-3-phosphate, isoleucine, valine, erythrose, 3-hydroxy-2-oxovalerate, 4-methyl-2-oxopentanoate, 2-methylbutyrylcarnitine, 3-hydroxybutyrate, tyrosine, glycine, kynurenate, xanthine, beta-hydroxypyruvate, 3-hydroxypropanoate, hexanoylcarnitine, urate, palmitoyl sphingomyelin, quinate, hippurate, catechol sulfate, margarate, 5alpha-androstan-3beta, adrenate, alpha-hydroxyisovalerate, cinnamoylglycine, dehydroisoandrosterone sulfate (DHEA-S), deoxycholate, glutamine, 17alpha-diol disulfate and subsets thereof. Additional biomarkers for use in combination with those disclosed herein include those disclosed in International Patent Application Publication No. WO 2009/014639 and U.S. application Ser. No. 12/218,980, filed Jul. 17, 2008, the entireties of which are hereby incorporated by reference herein. In one aspect, the biomarkers correlate to type 2 diabetes.

Biomarkers for use in methods disclosed herein relating to predicting development of cardiovascular disease include those markers listed in Table 3 and Table 4 and subsets thereof. In one embodiment the biomarkers include 3-indoxylsulfate, propionylcarnitine, 3-dehydrocarnitine, acetylcarnitine, oleoylcarnitine, myo-inositol, 5alpha-pregnan-3beta, 20alpha-diol disulfate, 5alpha-pregnan-3alpha, 20beta-diol disulfate, xanthine, trigonelline (N'-methylnicotinate), 2-hydroxyhippurate (salicylurate), piperidine, 1-methylurate, 1,3-dimethylurate, 1,7-dimethylurate, 1,3,7-trimethylurate, kynurenine, and subsets thereof. In one aspect the biomarkers correlate to cardiovascular disease. Additional biomarkers for use in combination with those disclosed herein include those disclosed in International Patent Application Publication No. WO 2009/014639 and U.S. application Ser. No. 12/218,980, filed Jul. 17, 2008, the entireties of which are hereby incorporated by reference herein. In an embodiment the cardiovascular disease is myocardial infarction and the biomarkers are selected from Table 3. In an embodiment the cardiovascular disease is stroke and the biomarkers are selected from Table 4. Additional biomarkers for use in combination with those disclosed herein include those disclosed in International Patent Application Publication No. WO 2009/014639 and U.S. application Ser. No. 12/218,980, filed Jul. 17, 2008, the entireties of which are hereby incorporated by reference herein.

Biomarkers for use in methods disclosed herein correlating to insulin resistance, type 2 diabetes and/or cardiovascular disease, such as being impaired insulin sensitive, insulin resistant, or pre-diabetic include one or more of those listed in Tables 1, 2, 3, and/or 4 and subsets thereof. In an embodiment the biomarkers include a combination of the biomarkers 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine for use in the methods disclosed here. In one embodiment, the biomarkers for use in the disclosed methods include a combination of 3-phenylpropionate (hydrocinnamate), 3-(4-hydroxyphenyl)lactate, indolelactate, 5-oxoproline, bradykinin-hydroxy-pro (3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, erythrose, glycerol-3-phosphate, isoleucine, valine, to predict the progression to type-2 diabetes. In another embodiment, the biomarkers for use in the disclosed methods include a combination of adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate to determine progression to cardiovascular disease. Such combinations can also be combined with clinical measurements or predictors of insulin resistance and/or type 2 diabetes, such as body mass index, fasting plasma insulin or C-peptide measurements. Examples of additional combinations that can be used in the methods disclosed herein include those provided in the Examples below.

In one embodiment, biomarkers for use in identifying subjects for treatment by the administration of insulin resistance therapeutics include one or more of those listed 3-phenylpropionate (hydrocinnamate), 3-(4-hydroxyphenyl)lactate, indolelactate, 5-oxoproline, bradykinin-hydroxy-pro (3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine. In still another example, biomarkers for use in identifying subjects for admission into clinical trials for the administration of test compositions for effectiveness in treating insulin resistance or related conditions, include one or more of those listed 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine.

Additional biomarkers for use in the methods disclosed herein include metabolites related to the biomarkers listed 2-hydroxybutyrate, 3-hydroxy-butyrate, 3-methyl-2-oxobutyric acid, arginine, betaine, 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine. In addition, such additional biomarkers may also be useful in combination and with clinical measures, for example as ratios of biomarkers and such additional clinical measures.

Any number of biomarkers may be used in the methods disclosed herein. That is, the disclosed methods may include the determination of the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, fifteen or more biomarkers, etc., including a combination of all of the biomarkers in Tables 1, 2, 3, 4 and/or 5. In another aspect, the number of biomarkers for use in the disclosed methods include the levels of about twenty-five or less biomarkers, twenty or less, fifteen or less, ten or less, nine or less, eight or less, seven or less, six or less, five or less biomarkers. In another aspect, the number of biomarkers for use in the disclosed methods includes the levels of one, two, three, four, five, six, seven, eight, nine, ten, eleven, twelve, thirteen, fourteen, fifteen, twenty, or twenty-five biomarkers.

The biomarkers disclosed herein may also be used to generate a risk score ("Disease Risk Score") to predict a subject's probability of being insulin resistant, type 2 diabetic, and/or having cardiovascular disease (including myocardial infarction or stroke) for use in any of the disclosed methods. Any method or algorithm can be used to generate a Disease Risk Score based on the biomarkers in Tables 1, 2, 3, 4 and/or 5 for use in the methods of the present disclosure.

The biomarkers, panels, and algorithms may provide sensitivity levels for detecting or predicting predisposition to insulin resistance, type 2 diabetes, and/or cardiovascular disease greater than conventional methods, such as the oral glucose tolerance test, fasting plasma glucose test, hemoglobin A1C (and estimated average glucose, eAG), fasting plasma insulin, fasting proinsulin, adiponectin, HOMA-IR, and the like. In some embodiments, the biomarkers, panels, and algorithms provided herein provide sensitivity levels greater than about 55%, 56%, 57%, 58%, 59%, 60% or greater.

In other embodiments, the biomarkers, panels, and algorithms disclosed herein may provide a specificity level for detecting or predicting insulin resistance, type 2 diabetes and/or cardiovascular disease in a subject greater than conventional methods such as the oral glucose tolerance test, fasting plasma glucose test, adiponectin, and the like. In some embodiments, the biomarkers, panels, and algorithms provided herein provide specificity levels greater than about 80%, 85%, 90%, or greater.

In addition, the methods disclosed herein using the biomarkers and models listed in the tables may be used in combination with clinical diagnostic measures of the respective conditions. Combinations with clinical diagnostics (such as oral glucose tolerance test, fasting plasma glucose test, free fatty acid measurement, hemoglobin A1C (and estimated average glucose, eAG) measurements, fasting plasma insulin measurements, fasting proinsulin measurements, fasting C-peptide measurements, glucose sensitivity (beta cell index) measurements, adiponectin measurements, uric acid measurements, systolic and diastolic blood pressure measurements, triglyceride measurements, triglyceride/HDL ratio, cholesterol (HDL, LDL) measurements, LDL/HDL ratio, waist/hip ratio, age, family history of diabetes (T1D and/or T2D), family history of cardiovascular disease) may facilitate the disclosed methods, or confirm results of the disclosed methods, (for example, facilitating or confirming diagnosis, monitoring progression or regression, and/or determining predisposition to pre-diabetes, dysglycemia, type-2 diabetes, and/or cardiovascular disease).

Any suitable method may be used to detect the biomarkers in a biological sample in order to determine the level(s) of the one or more biomarkers. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof (e.g. LC-MS-MS). Further, the level(s) of the one or more biomarkers may be detected indirectly, for example, by using an assay that measures the level of a compound (or compounds) that correlates with the level of the biomarker(s) that are desired to be measured.

In some embodiments, the biological samples for use in the detection of the biomarkers are transformed into analytical samples prior to the analysis of the level or detection of the biomarker in the sample. For example, in some embodiments, protein extractions may be performed to transform the sample prior to analysis by, for example, liquid chromatography (LC) or tandem mass spectrometry (MS-MS), or combinations thereof. In other embodiments, the samples may be transformed during the analysis, for example by tandem mass spectrometry methods.

A. Diagnostic Methods

The biomarkers described herein may be used to diagnose, or to aid in diagnosing, whether a subject has a disease or condition, such as being insulin resistant, dysglycemic, type 2 diabetic and/or having cardiovascular disease. For example, biomarkers for use in diagnosing, or aiding in diagnosing, whether a subject is insulin resistant include one or more of those identified biomarkers in Tables 1, 2, 5. In one embodiment, the biomarkers include one or more of those identified in Tables 1, 2, 5, and combinations thereof. Any biomarker listed in Tables 1, 2, 5 may be used in the diagnostic methods, as well as any combination of the biomarkers listed in Tables 1, 2, 5, or combinations thereof.

Methods for diagnosing, or aiding in diagnosing, whether a subject has a disease or condition, such as being insulin resistant or having an insulin resistance related disorder, may be performed using one or more of the biomarkers identified Table 1, 2, 3, 4, and/or 5. A method of diagnosing (or aiding in diagnosing) whether a subject has a disease or condition, such as being insulin resistant, comprises (1) analyzing a biological sample from a subject to determine the level(s) of one or more biomarkers of insulin resistance listed 2-hydroxybutyrate, 3-hydroxy-butyrate, 3-methyl-2-oxo-butyric acid, arginine, betaine, 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine in the sample and (2) comparing the level(s) of the one or more biomarkers in the sample to insulin-resistance-positive and/or insulin-resistance-negative reference levels of the one or more biomarkers in order to diagnose (or aid in the diagnosis of) whether the subject is insulin resistant. When such a method is used in aiding in the diagnosis of a disease or condition, such as insulin resistance or pre-diabetes, the results of the method may be used along with other methods (or the results thereof) useful in the clinical determination of whether a subject has a given disease or condition. Methods useful in the clinical determination of whether a subject has a disease or condition such as insulin resistance or pre-diabetes are known in the art. For example, methods useful in the clinical determination of whether a subject is insulin resistant or is at risk of being insulin resistant include, for example, glucose disposal rates (Rd, M-wbm, M-ffm), body weight measurements, waist circumference measurements, BMI determinations, waist/hip ratio, triglycerides measurements, cholesterol (HDL, LDL) measurements, LDL/HDL ratio, triglyceride/HDL ratio, age, family history of diabetes (T1D and/or T2D), family history of cardiovascular disease, Peptide YY measurements, C-peptide measurements, Hemoglobin A1C measurements and estimated average glucose, (eAG), adiponectin measurements, fasting plasma glucose measurements (e.g., oral glucose tolerance test, fasting plasma glucose test), free fatty acid measurements, fasting plasma insulin and pro-insulin measurements, systolic and diastolic blood pressure measurements, urate measurements and the like. Methods useful for the clinical determination of whether a subject has insulin resistance include the hyperinsulinemic euglycemic clamp (HI clamp).

Independent studies were carried out to identify a set of biomarkers that when used with a polynomic algorithm enables the early detection of changes in insulin resistance in a subject. In one aspect, the biomarkers provided herein can be used to provide a physician with a probability score ("Disease Risk (DR) Score") indicating the probability that a subject is insulin resistant. The score is based upon clinically significant changed reference level(s) for a biomarker and/or combination of biomarkers. The reference level can be derived from an algorithm or computed from indices for impaired glucose disposal. The DR Score places the subject in the range of insulin resistance from normal (i.e. insulin sensitive) to insulin resistant to highly resistant. Disease progression or remission can be monitored by periodic determination and monitoring of the DR Score. Response to therapeutic intervention can be determined by monitoring the DR Score. The DR Score can also be used to evaluate drug efficacy.

Thus, the disclosure also provides methods for determining a subject's Disease Risk score (DR score) that may be performed using one or more of the biomarkers identified 2-hydroxybutyrate, 3-hydroxy-butyrate, 3-methyl-2-oxo-butyric acid, arginine, betaine, creatine, decanoyl carnitine, docosatetraenoic acid, glutamic acid, glycine, linoleic acid, linolenic acid, margaric acid, octanoyl carnitine, oleic acid, oleoyl-LPC, palmitate, palmitoleic acid, palmitoyl-LPC, serine, stearate, threonine, tryptophan, linoleoyl-LPC, 1,5-anhydroglucitol, stearoyl-LPC, glutamyl valine, gamma-glutamyl-leucine, heptadecenoic acid, alpha-ketobutyrate, cysteine, urate or a model using such biomarkers. For example, a method for determining the DR score of a subject comprises the steps of: (1) analyzing a biological sample from a subject to determine the level(s) of one or more insulin resistance biomarkers 2-hydroxybutyrate, 3-hydroxy-butyrate, 3-methyl-2-oxo-butyric acid, arginine, betaine, creatine, decanoyl carnitine, docosatetraenoic acid, glutamic acid, glycine, linoleic acid, linolenic acid, margaric acid, octanoyl carnitine, oleic acid, oleoyl-LPC, palmitate, palmitoleic acid, palmitoyl-LPC, serine, stearate, threonine, tryptophan, linoleoyl-LPC, 1,5-anhydroglucitol, stearoyl-LPC, glutamyl valine, gamma-glutamyl-leucine, heptadecenoic acid, alpha-ketobutyrate, cysteine, urate in the sample, and (2) comparing the level(s) of the one or more insulin resistance biomarkers in the sample to insulin resistance reference levels of the one or more biomarkers in order to determine the subject's insulin resistance score. The method may employ any number of markers selected from those listed 2-hydroxybutyrate, 3-hydroxy-butyrate, 3-methyl-2-oxo-butyric acid, arginine, betaine, creatine, decanoyl carnitine, docosatetraenoic acid, glutamic acid, glycine, linoleic acid, linolenic acid, margaric acid, octanoyl carnitine, oleic acid, oleoyl-LPC, palmitate, palmitoleic acid, palmitoyl-LPC, serine, stearate, threonine, tryptophan, linoleoyl-LPC, 1,5-anhydroglucitol, stearoyl-LPC, glutamyl valine, gamma-glutamyl-leucine, heptadecenoic acid, alpha-ketobutyrate, cysteine, urate, including 1, 2, 3, 4, 5, 6, 7, 8, 9, 10, or more markers. Multiple biomarkers may be correlated with a given condition, such as being insulin resistant, by any method, including statistical methods such as regression analysis.

Any suitable method may be used to analyze the biological sample in order to determine the level(s) of the one or more biomarkers in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured.

After the level(s) of the one or more biomarker(s) is determined, the level(s) may be compared to disease or condition reference level(s) or reference curves of the one or more biomarker(s) to determine a rating for each of the one or more biomarker(s) in the sample. The rating(s) may be aggregated using any algorithm to create a score, for example, a Disease Risk (DR) score, for the subject. The algorithm may take into account any factors relating to the disease or condition, such as having a family history of type 2 diabetes, including the number of biomarkers, the correlation of the biomarkers to the disease or condition, etc.

In one example, the subject's predicted disease risk level may be used to determine the probability that the subject is insulin resistant, type 2 diabetic, and/or has cardiovascular disease (i.e. determine the subject's DR Score). For example, using a standardized curve generated using one or more biomarkers (e.g., selected from 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine), a subject predicted to have a DR level of 9, may have a 10% probability of being a type 2 diabetic. Alternatively, in another example, a subject predicted to have a DR level of 3 may have a 90% probability of being type 2 diabetic.

B. Determining Predisposition to a Disease or Condition

The biomarkers identified herein may also be used in the determination of whether a subject not exhibiting any symptoms of a disease or condition, such as insulin resistance, dysglycemia, type 2 diabetes and/or cardiovascular disease, is predisposed to developing such a condition. The biomarkers may be used, for example, to determine whether a subject is predisposed to developing or becoming, for example, insulin resistant. Such methods of determining whether a subject having no symptoms of a particular disease or condition such as, impaired insulin sensitivity, being insulin resistant, or having type 2 diabetes, and/or cardiovascular disease, is predisposed to developing a particular disease or condition comprise (1) analyzing a biological sample from a subject to determine the level(s) of one or more biomarkers listed in Tables 1, 2, 3, 4 and/or 5 and combinations of the biomarkers 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicyluratc), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine in the sample and (2) comparing the level(s) of the one or more biomarkers in the sample to disease- or condition-positive and/or disease- or condition-negative reference levels of the one or more biomarkers in order to determine whether the subject is predisposed to developing the respective disease or condition. For example, the identification of biomarkers for cardiovascular disease allows for the determination of whether a subject having no symptoms of cardiovascular disease is predisposed to developing cardiovascular disease. A method of determining whether a subject having no symptoms of cardiovascular disease is predisposed to developing cardiovascular disease comprises (1) analyzing a biological sample from a subject to determine the level(s) of one or more biomarkers listed in Tables 3 and/or 4 and/or combinations of the biomarkers: adrenate; alpha-hydroxy-isovalerate; glutamine; glycine; tyrosine; deoxycholate; cinnamoylglycine; dehydroisoandrosterone sulfate (DHEA-S); 5alpha-androstan-3beta, 17alpha-diol disulfate; urate; 3-indoxylsulfate; propionylcarnitine; 3-dehydrocarnitine; acetylcarnitine; oleoylcarnitine; myo-inositol; 5alpha-pregnan-3beta, 20alpha-diol disulfate; xanthine; trigonelline (N'-methylnicotinate); 2-hydroxyhippurate (salicylurate); piperine; 1-methylurate; 1,3-dimethylurate; 1,7-dimethylurate; 1,3,7-trimethylurate; kynurenine; in the sample and (2) comparing the level(s) of the one or more biomarkers in the sample to cardiovascular disease-positive and/or cardiovascular disease-negative reference levels of the one or more biomarkers in order to determine whether the subject is predisposed to developing cardiovascular disease. The results of the method may be used along with other methods (or the results thereof) useful in the clinical determination of whether a subject is predisposed to developing the disease or condition.

After the level(s) of the one or more biomarkers in the sample are determined, the level(s) are compared to disease- or condition-positive and/or disease- or condition-negative reference levels in order to predict whether the subject is predisposed to developing a disease or condition such as insulin resistance, type-2 diabetes or cardiovascular disease. Levels of the one or more biomarkers in a sample corresponding to the disease- or condition-positive reference levels (e.g., levels that are the same as the reference levels, substantially the same as the reference levels, above and/or below the minimum and/or maximum of the reference levels, and/or within the range of the reference levels) are indicative of the subject being predisposed to developing the disease or condition. Levels of the one or more biomarkers in a sample corresponding to disease- or condition-negative reference levels (e.g., levels that are the same as the reference levels, substantially the same as the reference levels, above and/or below the minimum and/or maximum of the reference levels, and/or within the range of the reference levels) are indicative of the subject not being predisposed to developing the disease or condition. In addition, levels of the one or more biomarkers that are differentially present (especially at a level that is statistically significant) in the sample as compared to disease- or condition-negative reference levels may be indicative of the subject being predisposed to developing the disease or condition. Levels of the one or more biomarkers that are differentially present (especially at a level that is statistically significant) in the sample as compared to disease-condition-positive reference levels are indicative of the subject not being predisposed to developing the disease or condition.

By way of example, after the level(s) of the one or more biomarkers in the sample are determined, the level(s) are compared to cardiovascular disease-positive and/or cardiovascular disease-negative reference levels in order to predict whether the subject is predisposed to developing cardiovascular disease. Levels of the one or more biomarkers in a sample corresponding to the cardiovascular disease-positive reference levels (e.g., levels that are the same as the reference levels, substantially the same as the reference levels, above and/or below the minimum and/or maximum of the reference levels, and/or within the range of the reference levels) are indicative of the subject being predisposed to developing cardiovascular disease. Levels of the one or more biomarkers in a sample corresponding to the cardiovascular disease-negative reference levels (e.g., levels that are the same as the reference levels, substantially the same as the reference levels, above and/or below the minimum and/or maximum of the reference levels, and/or within the range of the reference levels) are indicative of the subject not being predisposed to developing cardiovascular disease. In addition, levels of the one or more biomarkers that are differentially present (especially at a level that is statistically significant) in the sample as compared to cardiovascular disease-negative reference levels are indicative of the subject being predisposed to developing cardiovascular disease. Levels of the one or more biomarkers that are differentially present (especially at a level that is statistically significant) in the sample as compared to cardiovascular disease-positive reference levels are indicative of the subject not being predisposed to developing insulin resistance.

Furthermore, it may also be possible to determine reference levels specific to assessing whether or not a subject that does not have a disease or condition such as insulin resistance, type 2 diabetes, or cardiovascular disease, is predisposed to developing a disease or condition. For example, it may be possible to determine reference levels of the biomarkers for assessing different degrees of risk (e.g., low, medium, high) in a subject for developing a disease or condition. Such reference levels could be used for comparison to the levels of the one or more biomarkers in a biological sample from a subject.

C. Monitoring Disease or Condition Progression/Regression

The identification of biomarkers herein allows for monitoring progression/regression of insulin resistance or related conditions in a subject. A method of monitoring the progression/regression insulin resistance or related condition (i.e., type-2 diabetes, impaired glucose tolerance (IGT), cardiovascular disease (CVD)) in a subject comprises (1) analyzing a first biological sample from a subject to determine the level(s) of one or more biomarkers listed in Tables 1, 2, 3, 4 and/or 5 and combinations thereof including 3-phenylpropionate (hydrocinnamate), 3-(4-hydroxyphenyl) lactate, indolelactate, 5-oxoproline, bradykinin-hydroxy-pro (3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine, and combinations thereof, in the first sample obtained from the subject at a first time point, (2) analyzing a second biological sample from a subject to determine the level(s) of the one or more biomarkers, the second sample obtained from the subject at a second time point, and (3) comparing the level(s) of one or more biomarkers in the first sample to the level(s) of the one or more biomarkers in the second sample in order to monitor the progression/regression of the disease or condition in the subject. The results of the method are indicative of the course of insulin resistance, type 2 diabetes, and/or cardiovascular disease (i.e., progression or regression, if any change) in the subject.

In one embodiment, the results of the method may be based on a Disease Risk (DR) Score which is representative of the probability of, for example, insulin resistance in the subject and which can be monitored over time. By comparing the DR Score from a first time point sample to the DR Score from at least a second time point sample, the progression or regression of insulin resistance can be determined. Such a method of monitoring the progression/regression of insulin resistance, type 2 diabetes and/or cardiovascular disease in a subject comprises (1) analyzing a first biological sample from a subject to determine an DR score for the first sample obtained from the subject at a first time point, (2) analyzing a second biological sample from a subject to determine a second DR score, the second sample obtained from the subject at a second time point, and (3) comparing the DR score in the first sample to the DR score in the second sample in order to monitor the progression/regression of insulin resistance, type-2 diabetes and/or cardiovascular disease in the subject. An increase in the probability of, for example, insulin resistance from the first to the second time point is indicative of the progression of insulin resistance in the subject, while a decrease in the probability from the first to the second time points is indicative of the regression of insulin resistance in the subject.

Using the biomarkers and algorithm of the instant invention for progression monitoring may guide, or assist a physician's decision to implement preventative measures such as dietary restrictions, exercise, and/or early-stage drug treatment.

D. Monitoring Therapeutic Efficacy

The biomarkers provided also allow for the assessment of the efficacy of a composition for treating a disease or condition such as insulin resistance, type 2 diabetes, or cardiovascular disease. For example, the identification of biomarkers for insulin resistance also allows for assessment of the efficacy of a composition for treating insulin resistance as well as the assessment of the relative efficacy of two or more compositions for treating insulin resistance. Such assessments may be used, for example, in efficacy studies as well as in lead selection of compositions for treating the disease or condition. In addition, such assessments may be used to monitor the efficacy of surgical procedures and/or lifestyle interventions on insulin resistance in a subject. Surgical procedures include bariatric surgery, while lifestyle interventions include diet modification or reduction, exercise programs, and the like.

Thus, in one such embodiment, provided are methods of assessing the efficacy of a composition for treating a disease or condition such as insulin resistance, type 2 diabetes or cardiovascular disease comprising (1) analyzing, from a subject (or group of subjects) having a disease or condition such as insulin resistance, type 2 diabetes or cardiovascular disease and currently or previously being treated with a composition, a biological sample (or group of samples) to determine the level(s) of one or more biomarkers for insulin resistance, type 2 diabetes or cardiovascular disease selected from the biomarkers listed in Tables 1, 2, 3, 4 and/or 5 and the biomarkers 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucineand (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) disease- or condition-positive reference levels of the one or more biomarkers, (c) disease- or condition-negative reference levels of the one or more biomarkers, (d) disease- or condition-progression-positive reference levels of the one or more biomarkers, and/or (e) disease- or condition-regression-positive reference levels of the one or more biomarkers. The results of the comparison are indicative of the efficacy of the composition for treating the respective disease or condition.

In another embodiment, methods of assessing the efficacy of a surgical procedure for treating a disease or condition such as insulin resistance, or related condition comprising (1) analyzing, from a subject (or group of subjects) having insulin resistance, type 2 diabetes or cardiovascular disease, and having previously undergone a surgical procedure, a biological sample (or group of samples) to determine the level(s) of one or more biomarkers for insulin resistance selected from the biomarkers listed in Tables 1, 2, 3, and/or 4 and the biomarkers 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine, and (2) comparing the level(s) of the one or more biomarkers in the sample to (a) level(s) of the one or more biomarkers in a previously-taken biological sample from the subject, wherein the previously-taken biological sample was obtained from the subject before undergoing the surgical procedure or taken immediately after undergoing the surgical procedure, (b) insulin resistance-positive (or type 2 diabetes-positive, cardiovascular disease-positive) reference levels of the one or more biomarkers, (c) insulin resistance-negative (or type 2 diabetes-negative, cardiovascular disease-negative) reference levels of the one or more biomarkers, (d) insulin resistance-progression-positive (or type 2 diabetes-progression positive, cardiovascular disease-progression-positive) reference levels of the one or more biomarkers, and/or (e) insulin resistance-regression-positive (or type 2 diabetes-regression positive, cardiovascular disease-regression-positive) reference levels of the one or more biomarkers. The results of the comparison are indicative of the efficacy of the surgical procedure for treating the respective disease or condition. In one embodiment, the surgical procedure is a gastro-intestinal surgical procedure, such as bariatric surgery.

The change (if any) in the level(s) of the one or more biomarkers over time may be indicative of progression or regression of the disease or condition in the subject. To characterize the course of a given disease or condition in the subject, the level(s) of the one or more biomarkers in the first sample, the level(s) of the one or more biomarkers in the second sample, and/or the results of the comparison of the levels of the biomarkers in the first and second samples may be compared to the respective disease- or condition-positive and/or disease- or condition-negative reference levels of the one or more biomarkers. If the comparisons indicate that the level(s) of the one or more biomarkers are increasing or decreasing over time (e.g., in the second sample as compared to the first sample) to become more similar to the disease- or condition-positive reference levels (or less similar to the disease- or condition-negative reference levels), then the results are indicative of the disease's or condition's progression. If the comparisons indicate that the level(s) of the one or more biomarkers are increasing or decreasing over time to become more similar to the disease- or condition-negative reference levels (or less similar to the disease- or condition-positive reference levels), then the results are indicative of the disease's or condition's regression.

For example, in order to characterize the course of insulin resistance in the subject, the level(s) of the one or more biomarkers in the first sample, the level(s) of the one or more biomarkers in the second sample, and/or the results of the comparison of the levels of the biomarkers in the first and second samples may be compared to insulin resistance-positive and/or insulin resistance-negative reference levels of the one or more biomarkers. If the comparisons indicate that the level(s) of the one or more biomarkers are increasing or decreasing over time (e.g., in the second sample as compared to the first sample) to become more similar to the insulin resistance-positive reference levels (or less similar to the insulin resistance-negative reference levels), then the results are indicative of insulin resistance progression. If the comparisons indicate that the level(s) of the one or more biomarkers are increasing or decreasing over time to become more similar to the insulin resistance-negative reference levels (or less similar to the insulin resistance-positive reference levels), then the results are indicative of insulin resistance regression.

The second sample may be obtained from the subject any period of time after the first sample is obtained. In one aspect, the second sample is obtained 1, 2, 3, 4, 5, 6, or more days after the first sample or after the initiation of the administration of a composition, surgical procedure, or lifestyle intervention. In another aspect, the second sample is obtained 1, 2, 3, 4, 5, 6, 7, 8, 9, 10, or more weeks after the first sample or after the initiation of the administration of a composition, surgical procedure, or lifestyle intervention. In another aspect, the second sample may be obtained 1, 2, 3, 4, 5, 6, 7, 8, 9, 10, 11, 12, or more months after the first sample or after the initiation of the administration of a composition, surgical procedure, or lifestyle intervention.

The course of a disease or condition such as being insulin resistant, or having type 2 diabetes, or cardiovascular disease in a subject may also be characterized by comparing the level(s) of the one or more biomarkers in the first sample, the level(s) of the one or more biomarkers in the second sample, and/or the results of the comparison of the levels of the biomarkers in the first and second samples to disease- or condition-progression-positive and/or disease- or condition-regression-positive reference levels. If the comparisons indicate that the level(s) of the one or more biomarkers are increasing or decreasing over time (e.g., in the second sample as compared to the first sample) to become more similar to the disease- or condition-progression-positive reference levels (or less similar to the disease- or condition-regression-positive reference levels), then the results are indicative of the disease or condition progression. If the comparisons indicate that the level(s) of the one or more biomarkers are increasing or decreasing over time to become more similar to the disease- or condition-regression-positive reference levels (or less similar to the disease- or condition-progression-positive reference levels), then the results are indicative of disease or condition regression.

As with the other methods described herein, the comparisons made in the methods of monitoring progression/regression of a disease or condition such as being insulin resistant, type 2 diabetic, or cardiovascular disease in a subject may be carried out using various techniques, including simple comparisons, one or more statistical analyses, and combinations thereof.

The results of the method may be used along with other methods (or the results thereof) useful in the clinical monitoring of progression/regression of the disease or condition in a subject.

As described above in connection with methods of diagnosing (or aiding in the diagnosis of) a disease or condition such as being insulin resistant, type 2 diabetic, or cardiovascular disease, any suitable method may be used to analyze the biological samples in order to determine the level(s) of the one or more biomarkers in the samples. In addition, the level(s) one or more biomarkers, including a combination of all of the biomarkers (Tables 1, 2, 3, 4, and/or 5, and/or the biomarkers 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine) or any fraction thereof, may be determined and used in methods of monitoring progression/regression of the respective disease or condition in a subject.

Such methods could be conducted to monitor the course of disease or condition development in subjects, for example the course of insulin resistance to type-2 diabetes and/or cardiovascular disease in a subject having pre-diabetes, or could be used in subjects not having a disease or condition (e.g., subjects suspected of being predisposed to developing the disease or condition) in order to monitor levels of predisposition to the disease or condition.

Clinical studies from around the world have been carried out to test whether anti-diabetic therapies, such as metformin or acarbose, can prevent diabetes progression in pre-diabetic patients. These studies have shown that such therapies can prevent diabetes onset. From the U.S. Diabetes Prevention Program (DPP), metformin reduced the rate of progression to diabetes by 38% and lifestyle and exercise intervention reduced the rate of progression to diabetes by 56%. Because of such successes, the ADA has revised its 2008 Standards of Medical Care in Diabetes to include the following statements in the section on Prevention/Delay of Type 2 Diabetes: "In addition to lifestyle counseling, metformin may be considered in those who are at very high risk (combined IFG and IGT plus other risk factors) and who are obese and under 60 years of age."

Pharmaceutical companies have carried out studies to assess whether certain classes of drugs, such as the PPARγ class of insulin sensitizers (e.g. muraglitozar), can prevent diabetes progression. Similar to the DPP trial, some of these studies have shown great promise and success for preventing diabetes, whereas others have exposed a certain amount of risk associated with certain anti-diabetic pharmacologic treatments when given to the general pre-diabetic population as defined by current insulin resistance diagnostics. Pharmaceutical companies are in need of diagnostics that can identify and stratify high risk pre-diabetics so they can assess the efficacy of their pre-diabetic therapeutic candidates more effectively and safely. In some embodiments, subjects that are identified as more insulin resistant or more predisposed to developing type 2 diabetes or cardiovascular disease may be more likely to respond to an insulin sensitizer composition.

Considering the infrequency of the oral glucose tolerance test (OGTT) procedures in the clinical setting, a new diagnostic test that directly measures insulin resistance, type 2 diabetes or cardiovascular disease in a fasted sample would enable a physician to identify and stratify patients who are moving toward the etiology of pre-diabetes, type-2 diabetes and cardiovascular disease much earlier.

E. Identification of Responders and Non-Responders to Therapeutic

The biomarkers provided also allow for the identification of subjects in whom the composition for treating a disease or condition such as insulin resistance, pre-diabetes, or type-2 diabetes is efficacious (i.e. patient responds to therapeutic). For example, the identification of biomarkers for insulin resistance also allows for assessment of the subject's response to a composition for treating insulin resistance as well as the assessment of the relative patient response to two or more compositions for treating insulin resistance. Such assessments may be used, for example, in selection of compositions for treating the disease or condition for certain subjects, or in the selection of subjects into a course of treatment or clinical trial.

Thus, also provided are methods of predicting the response of a patient to a composition for treating a disease or condition such as insulin resistance, pre-diabetes, or type-2 diabetes comprising (1) analyzing, from a subject (or group of subjects) having a disease or condition such as insulin resistance, pre-diabetes, or type-2 diabetes and currently or previously being treated with a composition, a biological sample (or group of samples) to determine the level(s) of one or more biomarkers for insulin resistance selected from the biomarkers listed in Tables 1, 2, 3 and/or 4 and one or more selected biomarkers listed 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionyl carnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine and (2) comparing the level(s) of the one or more biomarkers in the sample to (a) level(s) of the one or more biomarkers in a previously-taken biological sample from the subject, wherein the previously-taken biological sample was obtained from the subject before being treated with the composition, (b) disease- or condition-positive reference levels of the one or more biomarkers, (c) disease- or condition-negative reference levels of the one or more biomarkers, (d) disease- or condition-progression-positive reference levels of the one or more biomarkers, and/or (e) disease- or condition-regression-positive reference levels of the one or more biomarkers. The results of the comparison are indicative of the response of the patient to the composition for treating the respective disease or condition.

The change (if any) in the level(s) of the one or more biomarkers over time may be indicative of response of the subject to the therapeutic. To characterize the course of a given therapeutic in the subject, the level(s) of the one or more biomarkers in the first sample, the level(s) of the one or more biomarkers in the second sample, and/or the results of the comparison of the levels of the biomarkers in the first and second samples may be compared to the respective disease- or condition-positive and/or disease- or condition-negative reference levels of the one or more biomarkers. If the comparisons indicate that the level(s) of the one or more biomarkers are increasing or decreasing over time (e.g., in the second sample as compared to the first sample) to become more similar to the disease- or condition-positive reference levels (or less similar to the disease- or condition-negative reference levels), then the results are indicative of the patient not responding to the therapeutic. If the comparisons indicate that the level(s) of the one or more biomarkers are increasing or decreasing over time to become more similar to the disease- or condition-negative reference levels (or less similar to the disease- or condition-positive reference levels), then the results are indicative of the patient responding to the therapeutic.

For example, in order to characterize the patient response to a therapeutic for insulin resistance, the level(s) of the one or more biomarkers in the first sample, the level(s) of the one or more biomarkers in the second sample, and/or the results of the comparison of the levels of the biomarkers in the first and second samples may be compared to insulin resistance-positive and/or insulin resistance-negative reference levels of the one or more biomarkers. If the comparisons indicate that the level(s) of the one or more biomarkers are increasing or decreasing over time (e.g., in the second sample as compared to the first sample) to become more similar to the insulin resistance-positive reference levels (or less similar to the insulin resistance-negative reference levels), then the results are indicative of non-response to the therapeutic. If the comparisons indicate that the level(s) of the one or more biomarkers are increasing or decreasing over time to become more similar to the insulin resistance-negative reference levels (or less similar to the insulin resistance-positive reference levels), then the results are indicative of response to the therapeutic.

The second sample may be obtained from the subject any period of time after the first sample is obtained. In one aspect, the second sample is obtained 1, 2, 3, 4, 5, 6, or more days after the first sample. In another aspect, the second sample is obtained 1, 2, 3, 4, 5, 6, 7, 8, 9, 10, or more weeks after the first sample or after the initiation of treatment with the composition. In another aspect, the second sample may be obtained 1, 2, 3, 4, 5, 6, 7, 8, 9, 10, 11, 12, or more months after the first sample or after the initiation of treatment with the composition.

As with the other methods described herein, the comparisons made in the methods of determining a patient response to a therapeutic for a disease or condition such as insulin resistance, pre-diabetes, or type-2 diabetes in a subject may be carried out using various techniques, including simple comparisons, one or more statistical analyses, and combinations thereof.

The results of the method may be used along with other methods (or the results thereof) useful in determining a patient response to a therapeutic for the disease or condition in a subject.

As described above in connection with methods of diagnosing (or aiding in the diagnosis of) a disease or condition such as insulin resistance, pre-diabetes, or type-2 diabetes, any suitable method may be used to analyze the biological samples in order to determine the level(s) of the one or more biomarkers in the samples. In addition, the level(s) one or more biomarkers, including a combination of all of the biomarkers 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, 3-indoxylsulfate, propionylcarnitine, 3-dehydrocarnitine, acetylcarnitine, oleoylcarnitine, myo-inositol, 5alpha-pregnan-3beta, 20alpha-diol disulfate, xanthine, trigonelline (N'-methylnicotinate), 2-hydroxyhippurate (salicylurate), piperine, 1-methylurate, 1,3-dimethylurate, 1,7-dimethylurate, 1,3,7-trimethylurate, kynurenine, 2-methylbutrylcarnitine, 3-hydroxy-2-oxovalerate, 3-hydroxybutyrate, 3-hydroxypropanoate, beta-hydroxypyruvate, catechol sulfate, erythrose, glycerol-3-phosphate, hexanoylcarnitine, hippurate, margarate, palmitoyl sphingomyelin, quinate, and isoleucine or any fraction thereof, may be determined and used in methods of monitoring progression/regression of the respective disease or condition in a subject.

Such methods could be conducted to monitor the patient response to a therapeutic for a disease or condition development in subjects, for example the course of pre-diabetes to type-2 diabetes in a subject having pre-diabetes, or could be used in subjects not having a disease or condition (e.g., subjects suspected of being predisposed to developing the disease or condition) in order to monitor levels of predisposition to the disease or condition.

Pharmaceutical companies have carried out studies to assess whether certain classes of drugs, such as the PPARγ class of insulin sensitizers, can prevent diabetes progression. Some of these studies have shown great promise and success for preventing diabetes, whereas others have exposed a certain amount of risk associated with certain anti-diabetic pharmacologic treatments when given to the general pre-diabetic population as defined by current IR diagnostics. Pharmaceutical companies are in need of diagnostics that can identify responders and non-responders in order to stratify high risk pre-diabetics to assess the efficacy of their pre-diabetic therapeutic candidates more effectively and safely. A new diagnostic test that discriminates non-responding from responding patients to a therapeutic would enable pharmaceutical companies to identify and stratify patients that are likely to respond to the therapeutic agent and target specific therapeutics for certain cohorts that are likely to respond to the therapeutic.

F. Other Methods

Other methods of using the biomarkers discussed herein are also contemplated. For example, the methods described in U.S. Pat. Nos. 7,005,255; 7,329,489; 7,550,258; 7,550,260; 7,553,616; 7,635,556; 7,682,782; and 7,682,784 may be conducted using a small molecule profile comprising one or more of the biomarkers disclosed herein.

EXAMPLES

I. General Methods

A. Identification of Metabolic Profiles

Each sample was analyzed to determine the concentration of several hundred metabolites. Analytical techniques such as GC-MS (gas chromatography-mass spectrometry) and LC-MS (liquid chromatography-mass spectrometry) were used to analyze the metabolites. Multiple aliquots were simultaneously, and in parallel, analyzed, and, after appropriate quality control (QC), the information derived from each analysis was recombined. Every sample was characterized according to several thousand characteristics, which ultimately amount to several hundred chemical species. The techniques used were able to identify novel and chemically unnamed compounds.

B. Statistical Analysis:

The data was analyzed using several statistical methods to identify molecules (either known, named metabolites or unnamed metabolites) present at differential levels in a definable population or subpopulation (e.g., biomarkers for insulin resistant biological samples compared to control biological samples or compared to insulin sensitive patients) useful for distinguishing between the definable populations (e.g., insulin resistance and control, insulin resistance and insulin sensitive, insulin resistance and type-2 diabetes). Other molecules (either known, named metabolites or unnamed metabolites) in the definable population or subpopulation were also identified.

Random forest analyses were used for classification of samples into groups (e.g. disease or healthy, insulin resistant or normal insulin sensitivity). Random forests give an estimate of how well we can classify individuals in a new data set into each group, in contrast to a t-test, which tests whether the unknown means for two populations are different or not. Random forests create a set of classification trees based on continual sampling of the experimental units and compounds. Then each observation is classified based on the majority votes from all the classification trees.

Regression analysis was performed using the Random Forest Regression method and the Univariate Correlation/Linear Regression method to build models that are useful to identify the biomarker compounds that are associated with disease or disease indicators (e.g. Rd) and then to identify biomarker compounds useful to classify individuals according to for example, the level of glucose utilization as normal, insulin impaired, or insulin resistant. Biomarker compounds that are useful to predict disease or measures of disease (e.g. Rd) and that are positively or negatively correlated with disease or measures of disease (e.g. Rd) were identified in these analyses. All of the biomarker compounds identified in these analyses were statistically significant ($p<0.05$, $q<0.1$).

Recursive partitioning relates a 'dependent' variable (Y) to a collection of independent ('predictor') variables (X) in order to uncover—or simply understand—the elusive relationship, $Y=f(X)$. The analysis was performed with the JMP program (SAS) to generate a decision tree. The statistical significance of the "split" of the data can be placed on a more quantitative footing by computing p-values, which discern the quality of a split relative to a random event. The significance level of each "split" of data into the nodes or branches of the tree was computed as p-values, which discern the quality of the split relative to a random event. It was given as LogWorth, which is the negative log 10 of a raw p-value.

Statistical analyses were performed with the program "R" available on the worldwide web at the website cran.r-project.org and in JMP 6.0.2 (SAS® Institute, Cary, N.C.).

Example 2

Biomarkers Useful for Predicting Disease Progression

A number of biomarkers useful to determine the insulin sensitive (IS) individuals who will develop type 2 diabetes (T2D), myocardial infarction (MI) or stroke were identified. The biomarkers were identified by collecting plasma samples at the time of study enrolment (baseline) from 543 non-diabetic, human subjects with a family history of diabetes who were followed for at least 7 to more than 10 years. Over the course of the study the participants fell into the following groups: 262 were "non-progressors" (i.e., subjects who remained stable and did not progress to IR, T2D or CVD (e.g., MI or stroke)), 131 subjects developed T2D ("T2D progressors"), 105 subjects had myocardial infarction (MI, "MI progressors"), 45 subjects had a stroke ("stroke progressors"). In brief, the plasma samples were extracted and split into equal parts for analysis on the GC/MS and LC/MS/MS platforms. Proprietary software was used to match ions to an in-house library of standards for metabolite identification and for metabolite quantitation by peak area integration. The resulting metabolomic profiles were statistically analyzed to identify the biomarkers that are differentially present between the groups using Welch's Two Sample t-test analysis.

Biomarkers which, when measured in human plasma, predict the development of type 2 diabetes within 3 years were identified. These biomarkers were present at different (higher or lower) levels at baseline in the plasma from participants that progressed to type 2 diabetes (N=131) within 3 years, compared to those subjects that did not progress to type 2 diabetes ("non-progressors", N=262). The biomarkers for predicting the progression to Type 2 diabetes in 3 years is presented in Table 1. Table 1 includes, for each listed biomarker, the biochemical name of the biomarker, an indication of the fold-change in the "Progressor" sample mean as compared to the "Non-Progressor" sample mean (values >1.0 represent an elevation in subjects who progress to T2D, and values <1.0 represent a lower level in the Progressors), the p-value, and the q-value determined in the statistical analysis of the data concerning the biomarkers. Also included in Table 1 are: the internal identifier for that biomarker compound in the in-house chemical library of authentic standards (CompID); the identifier for that biomarker compound in the Kyoto Encyclopedia of Genes and Genomes (KEGG), if available; and the identifier for that biomarker compound in the Human Metabolome Database (HMDB), if available.

TABLE 1

Biomarkers for predicting progression to Type 2 Diabetes in 3 years.

| Biomarker | T2D-3 yr Progressor/non-Progressor | p-value | q-value | CompID | KEGG ID | HMDB ID |
| --- | --- | --- | --- | --- | --- | --- |
| glycine | 0.88 | 0.0452 | 0.4401 | 32338 | C00037 | 00123 |
| glutamine | 0.64 | 0.0401 | 0.3991 | 53 | C00064 | 00641 |
| 3-phenylpropionate (hydrocinnamate) | 0.57 | 0.0176 | 0.2796 | 15749 | C05629 | 00764 |
| 3-methyl-2-oxobutyrate | 0.97 | 0.0246 | 0.3406 | 21047 | C00141 | 00019 |
| 5-oxoproline | 0.85 | 0.0308 | 0.3791 | 1494 | C01879 | 00267 |
| bradykinin, hydroxy-pro(3) | 0.69 | 0.0271 | 0.3438 | 33962 | | 11728 |
| bradykinin, des-arg(9) | 0.66 | 0.0395 | 0.3991 | 34420 | C00306 | 04246 |
| HXGXA | 0.73 | <0.001 | 0.0111 | 31534 | | |
| HWESASXX | 0.47 | <0.001 | 0.0017 | 32836 | | |
| XHWESASXXR | 0.58 | 0.0096 | 0.2050 | 31538 | | |
| [H]HWESASLLR[OH] | 0.62 | 0.0381 | 0.3991 | 33964 | | |
| phosphate | 0.91 | 0.0383 | 0.3991 | 11438 | C00009 | 01429 |
| n-Butyl Oleate | 0.70 | 0.0270 | 0.3438 | 36802 | | |
| 1-linoleoylglycerophosphocholine | 0.82 | <0.001 | 0.0256 | 34419 | C04100 | |
| palmitoyl sphingomyelin | 0.88 | 0.0387 | 0.3991 | 37506 | | |
| 5alpha-androstan-3beta,17alpha-diol disulfate | 0.81 | <0.001 | 0.0000 | 37187 | | |
| heme | 0.30 | 0.0403 | 0.3991 | 32593 | C00032 | 03178 |
| iminodiacetate (IDA) | 0.54 | 0.0064 | 0.1699 | 35837 | | 11753 |
| N-acetylthreonine | 1.24 | 0.0052 | 0.1532 | 33939 | C01118 | |
| tyrosine | 1.18 | 0.0355 | 0.3991 | 1299 | C00082 | 00158 |
| 3-(4-hydroxyphenyl)lactate | 1.34 | 0.0116 | 0.2291 | 32197 | C03672 | 00755 |
| indolelactate | 1.26 | 0.0241 | 0.3406 | 18349 | C02043 | 00671 |
| valine | 1.07 | 0.0395 | 0.3991 | 1649 | C00183 | 00883 |
| 3-hydroxyisobutyrate | 1.35 | <0.001 | 0.0304 | 1549 | C06001 | 00336 |
| 2-hydroxybutyrate (AHB) | 1.18 | 0.0145 | 0.2614 | 21044 | C05984 | 00008 |
| mannose | 1.14 | 0.0167 | 0.2721 | 584 | C00159 | 00169 |
| trehalose | 1.51 | 0.0064 | 0.1699 | 15573 | C01083 | 00975 |
| glucose | 1.14 | 0.0029 | 0.1059 | 20488 | C00293 | 00122 |
| succinate | 1.10 | 0.0140 | 0.2614 | 1437 | C00042 | 00254 |
| 1-oleoylglycerophosphoinositol | 1.07 | 0.0112 | 0.2291 | 36602 | | |
| urate | 1.21 | <0.001 | 0.0087 | 1604 | C00366 | 00289 |

Biomarkers which, when measured in human plasma, predict the development of T2D in 5 years were identified. These biomarkers were present at different (higher or lower) levels at baseline in the plasma from participants who developed T2D in 5 years ("progressors", N=131), compared to those subjects that did not ("non-progressors", N=262). The biomarkers of progression to T2D in 5 years are presented in Table 2. Table 2 includes, for each listed biomarker, the biochemical name of the biomarker, an indication of the fold-change in the "Progressor" sample mean as compared to the "Non-Progressor" sample mean (values >1.0 represent an elevation in subjects who progress to T2D, and values <1.0 represent lower levels in the Progressors), the p-value, and the q-value determined in the statistical analysis of the data concerning the biomarkers. Also included in Table 2 are: the internal identifier for that biomarker compound in the in-house chemical library of authentic standards (CompID); the identifier for that biomarker compound in the Kyoto Encyclopedia of Genes and Genomes (KEGG), if available; and the identifier for that biomarker compound in the Human Metabolome Database (HMDB), if available.

TABLE 2

Biomarkers for predicting progression to Type 2 Diabetes in 5 years.

| Biomarker | T2D-5 yr Progressor/non-Progressor | p-value | q-value | CompID | KEGG ID | HMDB ID |
| --- | --- | --- | --- | --- | --- | --- |
| 3-phenylpropionate (hydrocinnamate) | 0.54 | <0.001 | 0.0012 | 15749 | C05629 | 00764 |
| 5-oxoproline | 0.90 | 0.0189 | 0.1727 | 1494 | C01879 | 00267 |
| bradykinin, hydroxy-pro(3) | 0.68 | <0.001 | 0.0255 | 33962 | | 11728 |
| phosphate | 0.95 | 0.0319 | 0.2186 | 11438 | C00009 | 01429 |
| 10-undecenoate (11:1n1) | 0.90 | 0.0388 | 0.2431 | 32497 | | |
| 2-hydroxypalmitate | 0.93 | 0.0193 | 0.1729 | 35675 | | |
| glycerol 3-phosphate (G3P) | 0.83 | <0.001 | 0.0190 | 15365 | C00093 | 00126 |
| glycerophosphorylcholine (GPC) | 0.89 | 0.0058 | 0.0945 | 15990 | C00670 | 00086 |
| 2-palmitoylglycerophosphoethanolamine | 0.81 | 0.0334 | 0.2253 | 35688 | | |
| 1-linoleoylglycerophosphoethanolamine | 0.86 | 0.0353 | 0.2332 | 32635 | | 11507 |
| 1-heptadecanoylglycerophosphocholine | 0.86 | 0.0294 | 0.2154 | 33957 | | 12108 |
| 1-oleoylglycerophosphocholine | 0.93 | 0.0130 | 0.1465 | 33960 | | |
| 1-linoleoylglycerophosphocholine | 0.85 | <0.001 | 0.0012 | 34419 | C04100 | |
| 1-arachidoylglycerophosphocholine | 0.86 | 0.0251 | 0.1902 | 35623 | | 10390 |

TABLE 2-continued

Biomarkers for predicting progression to Type 2 Diabetes in 5 years.

| Biomarker | T2D-5 yr Progressor/ non-Progressor | p-value | q-value | CompID | KEGG ID | HMDB ID |
|---|---|---|---|---|---|---|
| dehydroisoandrosterone sulfate (DHEA-S) | 0.79 | 0.0142 | 0.1469 | 32425 | C04555 | 01032 |
| epiandrosterone sulfate | 0.83 | 0.0167 | 0.1565 | 33973 | C07635 | 00365 |
| 4-androsten-3beta,17beta-diol disulfate | 0.86 | 0.0307 | 0.2158 | 37203 | | 03818 |
| 5alpha-androstan-3beta,17alpha-diol disulfate | 0.85 | 0.0011 | 0.0351 | 37187 | | |
| threonate | 0.86 | 0.0139 | 0.1469 | 27738 | C01620 | 00943 |
| heme | 0.37 | 0.0020 | 0.0544 | 32593 | C00032 | 03178 |
| biliverdin | 0.82 | 0.0168 | 0.1565 | 2137 | C00500 | 01008 |
| catechol sulfate | 0.83 | 0.0365 | 0.2355 | 35320 | C00090 | |
| glycerol 2-phosphate | 0.86 | 0.0165 | 0.1565 | 27728 | C02979, D01488 | 02520 |
| thymol sulfate | 0.61 | 0.0403 | 0.2489 | 36095 | C09908 | 01878 |
| cinnamoylglycine | 0.75 | 0.0024 | 0.0622 | 38637 | | |
| tyrosine | 1.08 | 0.0373 | 0.2371 | 1299 | C00082 | 00158 |
| 3-(4-hydroxyphenyl)lactate | 1.21 | <0.001 | 0.0266 | 32197 | C03672 | 00755 |
| indolelactate | 1.13 | 0.0234 | 0.1865 | 18349 | C02043 | 00671 |
| isoleucine | 1.10 | <0.001 | 0.0255 | 1125 | C00407 | 00172 |
| valine | 1.07 | 0.0052 | 0.0908 | 1649 | C00183 | 00883 |
| alpha-hydroxyisovalerate | 1.16 | 0.0065 | 0.1022 | 33937 | | 00407 |
| 2-hydroxybutyrate (AHB) | 1.17 | <0.001 | 0.0255 | 21044 | C05984 | 00008 |
| bradykinin, des-arg(9) | 1.14 | 0.0211 | 0.1813 | 34420 | C00306 | 04246 |
| [H]HWESASLLR[OH] | 1.30 | 0.0472 | 0.2721 | 33964 | | |
| erythrose | 1.18 | 0.0048 | 0.0877 | 27722 | C01796 | 02649 |
| mannose | 1.12 | 0.0032 | 0.0704 | 584 | C00159 | 00169 |
| glucose | 1.15 | <0.001 | 0.0000 | 20488 | C00293 | 00122 |
| succinate | 1.09 | 0.0092 | 0.1229 | 1437 | C00042 | 00254 |
| stearidonate (18:4n3) | 1.17 | 0.0415 | 0.2497 | 33969 | C16300 | 06547 |
| adrenate (22:4n6) | 1.15 | 0.0144 | 0.1469 | 32980 | C16527 | 02226 |
| deoxycholate | 1.20 | 0.0414 | 0.2497 | 1114 | C04483 | 00626 |
| 7-alpha-hydroxy-3-oxo-4-cholestenoate (7-Hoca) | 1.31 | <0.001 | 0.0255 | 36776 | C17337 | 12458 |
| urate | 1.10 | 0.0040 | 0.0822 | 1604 | C00366 | 00289 |

Biomarkers which, when measured in human plasma, predict the development of myocardial infarction (MI) were identified. These biomarkers were present at different (higher or lower) levels in the plasma at baseline from participants that had a myocardial infarction (MI) ("progressors", N=105), compared to those subjects that did not suffer a myocardial infarction (MI) ("non-progressors", N=262). The biomarkers of progression to myocardial infarction are presented in Table 3. Table 1 includes, for each listed biomarker, the biochemical name of the biomarker, an indication of the fold-change in the "Progressor" sample mean as compared to the "Non-Progressor" sample mean (values >1.0 represent an elevation in subjects who progress to MI, and values <1.0 represent a lower level in the Progressors), the p-value, and the q-value determined in the statistical analysis of the data concerning the biomarkers. Also included in Table 3 are: the internal identifier for that biomarker compound in the in-house chemical library of authentic standards (CompID); the identifier for that biomarker compound in the Kyoto Encyclopedia of Genes and Genomes (KEGG), if available; and the identifier for that biomarker compound in the Human Metabolome Database (HMDB), if available.

TABLE 3

Biomarkers for predicting progression to Myocardial Infarction.

| Biomarker | MI Progressor/ non-Progressor | p-value | q-value | CompID | KEGG ID | HMDB ID |
|---|---|---|---|---|---|---|
| glycine | 0.94 | 0.0390 | 0.0986 | 32338 | C00037 | 00123 |
| N-acetylglycine | 0.86 | 0.0196 | 0.0639 | 27710 | | 00532 |
| serine | 0.96 | 0.0397 | 0.0996 | 32315 | C00065 | 03406 |
| glutamine | 0.78 | 0.0081 | 0.0374 | 53 | C00064 | 00641 |
| HXGXA | 0.69 | 0.0039 | 0.0265 | 31534 | | |
| ADSGEGDFXAEGGGVR | 0.86 | 0.0359 | 0.0935 | 33084 | | |
| glycerate | 0.91 | 0.0019 | 0.0208 | 1572 | C00258 | 00139 |
| heptanoate (7:0) | 0.95 | 0.0423 | 0.1050 | 1644 | C17714 | 00666 |
| caprylate (8:0) | 0.93 | 0.0014 | 0.0187 | 32492 | C06423 | 00482 |
| caprate (10:0) | 0.94 | 0.0069 | 0.0345 | 1642 | C01571 | 00511 |
| 10-undecenoate (11:1n1) | 0.93 | 0.0315 | 0.0853 | 32497 | | |
| laurate (12:0) | 0.95 | 0.0020 | 0.0208 | 1645 | C02679 | 00638 |
| 5-dodecenoate (12:1n7) | 0.88 | 0.0184 | 0.0618 | 33968 | | 00529 |
| stearate (18:0) | 0.95 | 0.0286 | 0.0811 | 1358 | C01530 | 00827 |

TABLE 3-continued

Biomarkers for predicting progression to Myocardial Infarction.

| Biomarker | MI Progressor/ non-Progressor | p-value | q-value | CompID | KEGG ID | HMDB ID |
|---|---|---|---|---|---|---|
| methyl palmitate (15 or 2) | 0.95 | 0.0262 | 0.0790 | 38768 | | |
| 17-methylstearate | 0.91 | 0.0085 | 0.0388 | 38296 | | |
| glycerophosphorylcholine (GPC) | 0.93 | 0.0104 | 0.0442 | 15990 | C00670 | 00086 |
| 1-linoleoylglycerophosphocholine | 0.94 | 0.0286 | 0.0811 | 34419 | C04100 | |
| 5alpha-pregnan-3beta,20alpha-diol disulfate | 0.54 | 0.0101 | 0.0442 | 37198 | | |
| 5alpha-pregnan-3alpha,20beta-diol disulfate | 0.56 | <0.001 | 0.0121 | 37201 | | |
| piperine | 0.74 | 0.0018 | 0.0208 | 33935 | C03882 | |
| betaine | 1.09 | 0.0077 | 0.0369 | 3141 | C00719 | 00043 |
| N-acetylalanine | 1.05 | 0.0484 | 0.1100 | 1585 | C02847 | 00766 |
| glutamate | 1.04 | 0.0050 | 0.0297 | 57 | C00025 | 03339 |
| pyroglutamine | 1.22 | <0.001 | 0.0067 | 32672 | | |
| phenyllactate (PLA) | 1.10 | 0.0137 | 0.0502 | 22130 | C05607 | 00779 |
| phenylalanine | 1.05 | <0.001 | 0.0053 | 64 | C00079 | 00159 |
| tyrosine | 1.06 | <0.001 | 0.0121 | 1299 | C00082 | 00158 |
| 3-(4-hydroxyphenyl)lactate | 1.13 | <0.001 | 0.0067 | 32197 | C03672 | 00755 |
| phenylacetylglutamine | 1.32 | <0.001 | 0.0067 | 35126 | C05597 | 06344 |
| kynurenine | 1.08 | 0.0034 | 0.0257 | 15140 | C00328 | 00684 |
| indolelactate | 1.10 | 0.0042 | 0.0270 | 18349 | C02043 | 00671 |
| C-glycosyltryptophan | 1.09 | <0.001 | 0.0001 | 32675 | | |
| 3-indoxyl sulfate | 1.17 | <0.001 | 0.0136 | 27672 | | 00682 |
| alpha-hydroxyisocaproate | 1.13 | 0.0167 | 0.0590 | 22132 | C03264 | 00746 |
| isoleucine | 1.06 | <0.001 | 0.0083 | 1125 | C00407 | 00172 |
| leucine | 1.05 | 0.0026 | 0.0241 | 60 | C00123 | 00687 |
| valine | 1.03 | 0.0173 | 0.0590 | 1649 | C00183 | 00883 |
| 2-methylbutyroylcarnitine | 1.10 | 0.0035 | 0.0257 | 35431 | | 00378 |
| dimethylarginine (SDMA + ADMA) | 1.05 | 0.0123 | 0.0475 | 36808 | C03626 | 01539, 03334 |
| ornithine | 1.14 | 0.0032 | 0.0257 | 35832 | C00077 | 03374 |
| urea | 1.12 | 0.0033 | 0.0257 | 1670 | C00086 | 00294 |
| citrulline | 1.08 | 0.0113 | 0.0464 | 2132 | C00327 | 00904 |
| creatinine | 1.04 | 0.0284 | 0.0811 | 513 | C00791 | 00562 |
| 4-guanidinobutanoate | 1.05 | 0.0457 | 0.1084 | 15681 | C01035 | 03464 |
| mannitol | 1.18 | 0.0114 | 0.0464 | 15335 | C00392 | 00765 |
| 1,5-anhydroglucitol (1,5-AG) | 1.07 | 0.0154 | 0.0552 | 20675 | C07326 | 02712 |
| lactate | 1.12 | 0.0054 | 0.0298 | 527 | C00186 | 00190 |
| succinate | 1.07 | 0.0017 | 0.0208 | 1437 | C00042 | 00254 |
| 3-carboxy-4-methyl-5-propyl-2-furanpropanoate (CMPF) | 1.29 | 0.0037 | 0.0257 | 31787 | | |
| 3-dehydrocarnitine | 1.06 | 0.0218 | 0.0677 | 32654 | C02636 | 12154 |
| palmitoylcarnitine | 1.08 | 0.0334 | 0.0884 | 22189 | C02990 | 00222 |
| oleoylcarnitine | 1.08 | 0.0280 | 0.0811 | 35160 | | 05065 |
| glycocholenate sulfate | 1.12 | 0.0473 | 0.1084 | 32599 | | |
| choline | 1.08 | <0.001 | 0.0002 | 15506 | C00114 | 00097 |
| myo-inositol | 1.07 | <0.001 | 0.0121 | 19934 | C00137 | 00211 |
| 2-palmitoylglycerophosphocholine | 1.08 | 0.0270 | 0.0803 | 35253 | | |
| 1-stearoylglycerophosphocholine | 1.05 | 0.0319 | 0.0853 | 33961 | | |
| 2-stearoylglycerophosphocholine | 1.05 | 0.0463 | 0.1084 | 35255 | | |
| 1-arachidoylglycerophosphocholine | 1.11 | 0.0197 | 0.0639 | 35623 | | 10390 |
| 1-stearoylglycerol (1-monostearin) | 1.04 | 0.0220 | 0.0677 | 21188 | D01947 | |
| 5alpha-androstan-3beta,17beta-diol disulfate | 1.19 | 0.0102 | 0.0442 | 37190 | | 00493 |
| xanthine | 1.29 | 0.0119 | 0.0472 | 3147 | C00385 | 00292 |
| pseudouridine | 1.06 | <0.001 | 0.0053 | 33442 | C02067 | 00767 |
| trigonelline (N'-methylnicotinate) | 1.30 | 0.0117 | 0.0471 | 32401 | C01004 | 00875 |
| 2-hydroxyhippurate (salicylurate) | 1.97 | 0.0054 | 0.0298 | 18281 | C07588 | 00840 |
| 4-vinylphenol sulfate | 1.24 | 0.0051 | 0.0297 | 36098 | C05627 | 04072 |
| 1-methylurate | 1.24 | 0.0011 | 0.0148 | 34395 | | 03099 |
| 1,3-dimethylurate | 1.21 | 0.0026 | 0.0241 | 32391 | | 01857 |
| 1,7-dimethylurate | 1.22 | 0.0173 | 0.0590 | 34400 | C16356 | 11103 |
| 1,3,7-trimethylurate | 1.18 | 0.0092 | 0.0411 | 34404 | C16361 | 02123 |
| erythritol | 1.09 | 0.0376 | 0.0969 | 20699 | C00503 | 02994 |

Biomarkers which, when measured in human plasma, predict the development of stroke were identified. These biomarkers were present at different (higher or lower) levels at baseline in the plasma from participants who developed a stroke ("progressors", N=45), compared to those subjects that did not ("non-progressors", N=262). The biomarkers of progression to stroke are presented in Table 4. Table 4 includes, for each listed biomarker, the biochemical name of the biomarker, an indication of the fold-change in the "Progressor" sample mean as compared to the "Non-Progressor" sample mean (values >1.0 represent an elevation in subjects who progress to Stroke, and values <1.0 represent a lower level in the Progressors), the p-value, and the q-value determined in the statistical analysis of the data concerning the biomarkers. Also included in Table 4 are: the internal identifier for that biomarker compound in the in-house chemical library of authentic standards (CompID); the identifier for that biomarker compound in the Kyoto Encyclopedia of Genes and Genomes (KEGG), if available; and the identifier for that biomarker compound in the Human Metabolome Database (HMDB), if available.

TABLE 4

Biomarkers for predicting progression to Stroke.

| Biomarker | Stroke Progressor/non-Progressor | p-value | q-value | CompID | KEGG ID | HMDS ID |
|---|---|---|---|---|---|---|
| anthranilate | 0.88 | 0.0184 | 0.1669 | 4970 | C00108 | 01123 |
| caproate (6:0) | 0.91 | 0.0370 | 0.2217 | 32489 | C01585 | 00535 |
| heptanoate (7:0) | 0.92 | 0.0096 | 0.1437 | 1644 | C17714 | 00666 |
| 3-hydroxyoctanoate | 0.91 | 0.0321 | 0.2062 | 22001 |  | 01954 |
| 8-hydroxyoctanoate | 0.89 | 0.0439 | 0.2468 | 21239 |  | 00711 |
| 2-hydroxystearate | 0.93 | 0.0403 | 0.2294 | 17945 | C03045 |  |
| 2-hydroxypalmitate | 0.93 | 0.0258 | 0.1875 | 35675 |  |  |
| azelate (nonanedioate) | 0.89 | 0.0253 | 0.1875 | 18362 | C08261 | 00784 |
| isovalerate | 0.91 | 0.0319 | 0.2062 | 34732 | C08262 | 00718 |
| glycerophosphorylcholine (GPC) | 0.91 | 0.0169 | 0.1669 | 15990 | C00670 | 00086 |
| dehydroisoandrosterone sulfate (DHEA-S) | 0.86 | 0.0311 | 0.2059 | 32425 | C04555 | 01032 |
| 5alpha-pregnan-3beta,20alpha-diol disulfate | 0.49 | <0.001 | 0.0451 | 37198 |  |  |
| 5alpha-pregnan-3alpha,20beta-diol disulfate | 0.46 | <0.001 | 0.0135 | 37201 |  |  |
| pregn steroid monosulfate | 0.82 | 0.0254 | 0.1875 | 32619 | C18044 | 00774 |
| arabonate | 0.87 | 0.0150 | 0.1669 | 37516 |  | 00539 |
| triethyleneglycol | 0.82 | 0.0046 | 0.0903 | 27743 |  |  |
| alanine | 1.05 | 0.0176 | 0.1669 | 32339 | C00041 | 00161 |
| N-acetylalanine | 1.09 | 0.0015 | 0.0606 | 1585 | C02847 | 00766 |
| glutamate | 1.04 | 0.0198 | 0.1669 | 57 | C00025 | 03339 |
| glutaroyl carnitine | 1.10 | 0.0028 | 0.0690 | 35439 |  | 13130 |
| C-glycosyltryptophan | 1.07 | 0.0018 | 0.0682 | 32675 |  |  |
| ornithine | 1.17 | 0.0085 | 0.1315 | 35832 | C00077 | 03374 |
| citrulline | 1.10 | 0.0178 | 0.1669 | 2132 | C00327 | 00904 |
| 4-acetamidobutanoate | 1.06 | 0.0333 | 0.2110 | 1558 | C02946 | 03681 |
| lactate | 1.21 | <0.001 | 0.0130 | 527 | C00186 | 00190 |
| citrate | 1.11 | 0.0108 | 0.1437 | 1564 | C00158 | 00094 |
| acetylphosphate | 1.08 | 0.0026 | 0.0690 | 15488 | C00227 | 01494 |
| propionylcarnitine | 1.26 | 0.0391 | 0.2283 | 32452 | C03017 | 00824 |
| deoxycarnitine | 1.05 | 0.0200 | 0.1669 | 36747 | C01181 | 01161 |
| 3-dehydrocarnitine | 1.16 | <0.001 | 0.0014 | 32654 | C02636 | 12154 |
| acetylcarnitine | 1.72 | 0.0358 | 0.2186 | 32198 | C02571 | 00201 |
| oleoylcarnitine | 1.23 | 0.0063 | 0.1146 | 35160 |  | 05065 |
| glycerol | 1.06 | 0.0338 | 0.2111 | 15122 | C00116 | 00131 |
| myo-inositol | 1.08 | <0.001 | 0.0290 | 19934 | C00137 | 00211 |
| 1-palmitoylglycerol (1-monopalmitin) | 1.04 | 0.0267 | 0.1904 | 21127 |  |  |
| 1-oleoylglycerol (1-monoolein) | 1.13 | 0.0045 | 0.0903 | 21184 |  | 11567 |
| palmitoyl sphingomyelin | 1.13 | <0.001 | 0.0451 | 37506 |  |  |
| stearoyl sphingomyelin | 1.12 | 0.0024 | 0.0690 | 19503 | C00550 | 01348 |
| lathosterol | 1.36 | 0.0227 | 0.1822 | 33488 | C01189 | 01170 |
| cholesterol | 1.10 | 0.0044 | 0.0903 | 63 | C00187 | 00067 |
| uridine | 1.06 | 0.0197 | 0.1669 | 606 | C00299 | 00296 |
| pseudouridine | 1.08 | <0.001 | 0.0014 | 33442 | C02067 | 00767 |
| bilirubin (E,E) | 1.18 | 0.0250 | 0.1875 | 32586 |  |  |
| trigonelline (N'-methylnicotinate) | 1.27 | 0.0142 | 0.1669 | 32401 | C01004 | 00875 |
| benzoate | 1.07 | 0.0030 | 0.0690 | 15778 | C00180 | 01870 |
| 4-vinylphenol sulfate | 1.15 | 0.0139 | 0.1669 | 36098 | C05627 | 04072 |
| 1,3,7-trimethylurate | 1.28 | 0.0446 | 0.2475 | 34404 | C16361 | 02123 |
| erythritol | 1.11 | 0.0297 | 0.2053 | 20699 | C00503 | 02994 |

In an independent experiment with a different cohort, a number of biomarkers useful to determine the non-diabetic individuals who will develop type 2 diabetes (T2D) were identified. The biomarkers were identified by collecting plasma samples at the time of study enrollment (baseline) from 660 non-diabetic, human subjects who were followed for 5 years. Over the course of the study the participants fell into the following groups: 440 were "non-progressors" (i.e., subjects who remained stable and did not progress to T2D) and 220 developed T2D ("T2D progressors"). In brief, the plasma samples were extracted and split into equal parts for analysis on the GC/MS and LC/MS/MS platforms as described in General Methods. Proprietary software was used to match ions to an in-house library of standards for metabolite identification and for metabolite quantification by peak area integration. A total of 695 metabolites were measured of which the structural identities of 402 were determined ("Named") and 293 were undetermined ("Unnamed"). The resulting metabolomic profiles were statistically analyzed to identify the biomarkers that are differentially present between the groups using Analysis of Variance (ANOVA) with contrasts and by Random Forest classification.

Biomarkers which, when measured in human plasma, predict the development of type 2 diabetes within 5 years were identified. At baseline, the biomarkers were present at different (higher or lower) levels in the plasma from participants that progressed to type 2 diabetes within 5 years ("Progressors"), compared to those subjects that did not progress to type 2 diabetes ("non-progressors"). The biomarkers for predicting the progression to Type 2 diabetes in 5 years validate the earlier results presented in Table 2 and are presented in Table 5.

These plasma biomarkers were evaluated for the ability to predict the individuals who will progress to Type 2 Diabetes using regression analysis. The biomarker candidates were ranked using Random Forest analyses according to their contribution to the ability to predict separation of participants that progressed to type 2 diabetes within 5 years ("progressors") compared to those subjects that did not progress to type 2 diabetes ("non-progressors"). The top identified biomarkers for predicting the progression to Type 2 diabetes in 5 years according to Random Forest classification are presented in Table 5. Table 5 includes, for each listed biomarker, the biochemical name of the biomarker, an indication of the fold-change in the "Progressor" sample mean as compared to the "Non-Progressor" sample mean (values >1.0 represent an elevation in subjects who progress to T2D, and values <1.0 represent a lower level in the Progressors), the p-value, and the q-value determined in the statistical analysis of the data concerning the biomarkers. Also included in Table 5 are: the internal identifier for that biomarker compound in the in-house chemical library of authentic standards (CompID); the identifier for that biomarker compound in the Kyoto Encyclopedia of Genes and Genomes (KEGG), if available; and the identifier for that biomarker compound in the Human Metabolome Database (HMDB), if available.

TABLE 5

Biomarkers for predicting progression to Type 2 Diabetes in 5 years.

| Biomarker | Fold-of-change T2D-5 yr Progressor/ non-Progressor | p-value | q-value | CompID | KEGG ID | HMDB ID |
|---|---|---|---|---|---|---|
| 3-methyl-2-oxovalerate | 1.13 | 2.00E−15 | 1.77E−13 | 15676 | C00671 | 03736 |
| 2-methylbutyrylcarnitine (C5) | 1.15 | 4.04E−11 | 7.69E−10 | 35431 | | 00378 |
| kynurenate | 1.15 | 0.0001 | 0.0003 | 1417 | C01717 | 00715 |
| mannose | 1.19 | 0.00E+0 | 0.00E+00 | 584 | C00159 | 00169 |
| alpha-ketoglutarate | 1.33 | 9.61E−09 | 7.75E−08 | 33453 | C00026 | 00208 |
| 2-hydroxybutyrate (AHB) | 1.24 | 1.44E−11 | 3.81E−10 | 21044 | C05984 | 00008 |
| 4-methyl-2-oxopentanoate | 1.13 | 2.00E−15 | 1.77E−13 | 22116 | C00233 | 00695 |
| alpha-ketobutyrate | 1.32 | 6.44E−12 | 2.08E−10 | 42107 | C00109 | 00005 |
| xanthine | 1.33 | 3.98E−11 | 7.69E−10 | 3147 | C00385 | 00292 |
| glycine | 0.88 | 3.25E−11 | 7.34E−10 | 32338 | C00037 | 00123 |
| arachidonate (20:4n6) | 1.13 | 1.35E−10 | 2.07E−09 | 1110 | C00219 | 01043 |
| valine | 1.08 | 2.84E−09 | 2.61E−08 | 1649 | C00183 | 00883 |
| stearidonate (18:4n3) | 1.24 | 3.51E−09 | 3.00E−08 | 33969 | C16300 | 06547 |
| creatine | 1.24 | 2.25E−10 | 3.11E−09 | 27718 | C00300 | 00064 |
| 3-hydroxyisobutyrate | 1.18 | 3.84E−12 | 1.52E−10 | 1549 | C06001 | 00336 |
| tyrosine | 1.11 | 2.63E−13 | 1.33E−11 | 1299 | C00082 | 00158 |
| carnitine | 1.07 | 4.24E−11 | 7.69E−10 | 15500 | C00318 | |
| alpha-hydroxyisocaproate | 1.17 | 2.25E−07 | 1.21E−06 | 22132 | C03264 | 00746 |
| glucose | 1.13 | 0.00E+0 | 0.00E+00 | 20488 | C00031 | 00122 |
| isovalerylcarnitine | 1.19 | 1.09E−11 | 3.18E−10 | 34407 | | 00688 |
| cyclo(leu-pro) | 1.4 | 1.24E−10 | 2.07E−09 | 37104 | | |
| palmitate (16:0) | 1.13 | 4.63E−10 | 5.60E−09 | 1336 | C00249 | 00220 |
| palmitoyl sphingomyelin | 0.9 | 2.25E−09 | 2.25E−08 | 37506 | | |
| dihomo-linolenate (20:3n3 or n6) | 1.14 | 1.30E−10 | 2.07E−09 | 35718 | C03242 | 02925 |
| beta-hydroxyisovalerate | 1.12 | 8.14E−06 | 3.19E−05 | 12129 | | 00754 |
| hexanoylcarnitine | 1.14 | 1.41E−08 | 1.08E−07 | 32328 | | 00705 |
| palmitoleate (16:1n7) | 1.26 | 3.18E−09 | 2.80E−08 | 33447 | C08362 | 03229 |
| 10-heptadecenoate (17:1n7) | 1.2 | 8.96E−09 | 7.44E−08 | 33971 | | |
| N-acetylmethionine | 0.92 | 4.99E−06 | 2.01E−05 | 1589 | C02712 | 11745 |
| pyruvate | 1.17 | 1.24E−07 | 7.37E−07 | 599 | C00022 | 00243 |
| oleate (18:1n9) | 1.12 | 5.75E−08 | 3.63E−07 | 1359 | C00712 | 00207 |
| isoleucine | 1.07 | 1.15E−07 | 6.96E−07 | 1125 | C00407 | 00172 |
| piperine | 1.42 | 4.35E−06 | 1.81E−05 | 33935 | C03882 | |
| leucine | 1.07 | 1.25E−08 | 9.77E−08 | 60 | C00123 | 00687 |
| beta-hydroxypyruvate | 1.2 | 0.0019 | 0.0038 | 15686 | C00168 | 01352 |
| cinnamoylglycine | 0.69 | 5.48E−07 | 2.74E−06 | 38637 | | |
| 3-methyl-2-oxobutyrate | 1.07 | 0.8276 | 0.4012 | 21047 | C00141 | 00019 |
| docosapentaenoate (n6 DPA; 22:5n6) | 1.22 | 1.87E−06 | 8.26E−06 | 37478 | C16513 | 13123 |
| gamma-glutamyltyrosine | 1.1 | 3.15E−10 | 4.16E−09 | 2734 | | |
| glycerol 3-phosphate (G3P) | 1.02 | 0.0005 | 0.0012 | 15365 | C00093 | 00126 |
| dihomo-linoleate (20:2n6) | 1.17 | 1.43E−07 | 8.00E−07 | 17805 | C16525 | |
| 3-(4-hydroxyphenyl)lactate | 1.16 | 2.67E−09 | 2.58E−08 | 32197 | C03672 | 00755 |
| gamma-glutamylphenylalanine | 1.1 | 1.66E−08 | 1.24E−07 | 33422 | | 00594 |
| 3-hydroxypropanoate | 1.14 | 1.67E−06 | 7.69E−06 | 42103 | C01013 | 00700 |
| pantothenate | 1.15 | 2.33E−07 | 1.23E−06 | 1508 | C00864 | 00210 |
| glutamate | 1.13 | 1.91E−08 | 1.35E−07 | 57 | C00025 | 03339 |
| alanine | 1.11 | 2.66E−08 | 1.76E−07 | 1126 | C00041 | 00161 |
| urate | 1.08 | 1.41E−07 | 8.00E−07 | 1604 | C00366 | 00289 |

TABLE 5-continued

Biomarkers for predicting progression to Type 2 Diabetes in 5 years.

| Biomarker | Fold-of-change T2D-5 yr Progressor/ non-Progressor | p-value | q-value | CompID | KEGG ID | HMDB ID |
|---|---|---|---|---|---|---|
| glycerol 2-phosphate | 0.96 | 0.0009 | 0.0021 | 27728 | C02979 | 02520 |
| propionylcarnitine | 1.13 | 1.79E−08 | 1.30E−07 | 32452 | C03017 | 00824 |
| tryptophan | 1.05 | 1.43E−05 | 5.18E−05 | 54 | C00078 | 00929 |
| 7-alpha-hydroxy-3-oxo-4-cholestenoate (7-Hoca) | 1.13 | 7.15E−07 | 3.52E−06 | 36776 | C17337 | 12458 |
| phenylalanine | 1.05 | 4.07E−06 | 1.71E−05 | 64 | C00079 | 00159 |
| bradykinin, hydroxy-pro(3) | 0.75 | 1.59E−09 | 1.71E−08 | 33962 | | 11728 |
| 4-androsten-3beta,17beta-diol disulfate 1* | 1.59 | 3.12E−06 | 1.35E−05 | 37202 | | 03818 |
| 1-linoleoylglycerophosphocholine | 0.9 | 5.35E−06 | 2.13E−05 | 34419 | C04100 | |
| catechol sulfate | 0.84 | 4.58E−07 | 2.37E−06 | 35320 | C00090 | |
| quinate | 0.79 | 0.0002 | 0.0007 | 18335 | C00296 | 03072 |
| docosapentaenoate (n3 DPA; 22:5n3) | 1.18 | 1.88E−06 | 8.26E−06 | 32504 | C16513 | 01976 |
| 2-linoleoylglycerophosphocholine | 0.85 | 1.72E−05 | 6.10E−05 | 35257 | | |
| hippurate | 0.81 | 1.71E−06 | 7.75E−06 | 15753 | C01586 | 00714 |
| glutamine | 0.95 | 6.44E−05 | 0.0002 | 53 | C00064 | 00641 |
| 2-aminobutyrate | 1.11 | 1.29E−06 | 6.15E−06 | 32348 | C02261 | 00650 |
| tryptophan betaine | 0.5 | 0.0011 | 0.0025 | 37097 | C09213 | |
| N-acetyltryptophan | 1.16 | 1.53E−06 | 7.17E−06 | 33959 | C03137 | |
| eicosenoate (20:1n9 or 11) | 1.15 | 7.82E−05 | 0.0002 | 33587 | | 02231 |
| butyrylcarnitine | 1.22 | 1.32E−07 | 7.67E−07 | 32412 | | |
| 3-phenylpropionate (hydrocinnamate) | 0.75 | 2.21E−05 | 7.55E−05 | 15749 | C05629 | 00764 |
| lactate | 1.1 | 5.26E−05 | 0.0002 | 527 | C00186 | 00190 |
| gluconate | 1.08 | 0.0075 | 0.0118 | 587 | C00257 | 00625 |
| hydroxybutyrylcarnitine | 1.24 | 3.60E−05 | 0.0001 | 33910 | | |
| hydrochlorothiazide | 1.44 | 1.14E−05 | 4.19E−05 | 39625 | C07041 | 01928 |
| isovalerate | 1.11 | 0.0104 | 0.0154 | 34732 | C08262 | 00718 |
| caffeine | 1.31 | 7.33E−05 | 0.0002 | 569 | C07481 | 01847 |
| asparagine | 0.95 | 0.0121 | 0.0173 | 34283 | C00152 | 00168 |
| stearate (18:0) | 1.09 | 9.64E−06 | 3.68E−05 | 1358 | C01530 | 00827 |
| 2-hydroxy-3-methylvalerate | 1.27 | 9.24E−06 | 3.58E−05 | 36746 | | 00317 |
| 1,3,7-trimethylurate | 1.26 | 0.0007 | 0.0017 | 34404 | C16361 | 02123 |
| 10-nonadecenoate (19:1n9) | 1.16 | 1.13E−05 | 4.19E−05 | 33972 | | |
| linoleate (18:2n6) | 1.06 | 0.0032 | 0.0059 | 1105 | C01595 | 00673 |
| gamma-glutamylglutamine | 0.92 | 2.24E−05 | 7.56E−05 | 2730 | | 11738 |
| maltotetraose | 1.46 | 0.0105 | 0.0154 | 15910 | C02052 | 01296 |
| 3-dehydrocarnitine* | 1.07 | 0.0118 | 0.017 | 32654 | C02636 | 12154 |
| 3-hydroxy-2-ethylpropionate | 1.09 | 0.0047 | 0.0081 | 32397 | | 00396 |
| taurocholate | 1.6 | 0.0004 | 0.001 | 18497 | C05122 | 00036 |
| adrenate (22:4n6) | 1.09 | 0.0004 | 0.001 | 32980 | C16527 | 02226 |
| fumarate | 1.06 | 0.0012 | 0.0026 | 1643 | C00122 | 00134 |
| trigonelline (N'-methylnicotinate) | 0.82 | 0.0022 | 0.0041 | 32401 | C01004 | 00875 |
| 2-hydroxyhippurate (salicylurate) | 5.02 | 0.3372 | 0.2298 | 18281 | C07588 | 00840 |
| 3-hydroxyhippurate | 0.8 | 0.0062 | 0.0101 | 39600 | | 06116 |
| campesterol | 0.84 | 0.0002 | 0.0005 | 39511 | C01789 | 02869 |
| indolepropionate | 0.79 | 0.0002 | 0.0005 | 32405 | | 02302 |
| 2-hydroxyglutarate | 1.06 | 0.0399 | 0.0462 | 37253 | C02630 | 00606 |
| methionine | 1.03 | 0.0053 | 0.009 | 1302 | C00073 | 00696 |
| gamma-glutamylleucine | 1.1 | 3.36E−06 | 1.43E−05 | 18369 | | 11171 |
| xylitol | 1.08 | 0.2375 | 0.1879 | 4966 | C00379 | 02917 |
| margarate (17:0) | 1.1 | 0.0002 | 0.0005 | 1121 | | 02259 |
| phenyllactate (PLA) | 1.1 | 0.0112 | 0.0164 | 22130 | C05607 | 00779 |
| acetylcarnitine | 1.09 | 0.0002 | 0.0005 | 32198 | C02571 | 00201 |
| 1-arachidonoylglycerophosphoinositol | 1.11 | 0.001 | 0.0023 | 34214 | | |
| lathosterol | 1.06 | 0.4008 | 0.2519 | 39864 | C01189 | 01170 |
| dodecanedioate | 0.98 | 0.085 | 0.0866 | 32388 | C02678 | 00623 |
| eicosapentaenoate (EPA; 20:5n3) | 1.14 | 0.0011 | 0.0024 | 18467 | C06428 | 01999 |
| 5-oxoproline | 0.94 | 0.0115 | 0.0166 | 1494 | C01879 | 00267 |
| malate | 1.09 | 0.0036 | 0.0065 | 1303 | C00149 | 00156 |
| pyroglutamine | 0.89 | 0.0006 | 0.0014 | 32672 | | |
| deoxycholate | 1.16 | 0.0019 | 0.0038 | 1114 | C04483 | 00626 |
| 5alpha-pregnan-3beta,20alpha-diol disulfate | 1.12 | 0.008 | 0.0124 | 37198 | | |
| 1,3-dihydroxyacetone | 1.13 | 0.0152 | 0.0209 | 35963 | C00184 | 01882 |
| linolenate [alpha or gamma; (18:3n3 or 6)] | 1.07 | 0.0047 | 0.0081 | 34035 | C06427 | 01388 |
| indoleacrylate | 0.9 | 0.0144 | 0.0199 | 22114 | | 00734 |
| inosine 5'-monophosphate (IMP) | 1.08 | 0.6603 | 0.348 | 2133 | C00130 | 00175 |
| serotonin (5HT) | 0.94 | 0.2798 | 0.2073 | 2342 | C00780 | 00259 |

TABLE 5-continued

Biomarkers for predicting progression to Type 2 Diabetes in 5 years.

| Biomarker | Fold-of-change T2D-5 yr Progressor/ non-Progressor | p-value | q-value | CompID | KEGG ID | HMDB ID |
|---|---|---|---|---|---|---|
| andro steroid monosulfate | 1.31 | 0.0001 | 0.0004 | 32792 | C04555 | 02759 |
| N-acetylphenylalanine | 1.14 | 0.0014 | 0.003 | 33950 | C03519 | 00512 |
| allantoin | 0.97 | 0.1396 | 0.1267 | 1107 | C02350 | 00462 |
| phosphoethanolamine | 0.91 | 0.0929 | 0.0926 | 12102 | C00346 | 00224 |
| 3-hydroxybutyrate (BHBA) | 1.03 | 0.448 | 0.2708 | 542 | C01089 | 00357 |
| leucylleucine | 1.28 | 0.0204 | 0.0267 | 36756 | C11332 | |
| methyl-beta-glucopyranoside | 0.58 | 0.0039 | 0.007 | 40480 | | |
| cortisone | 1.05 | 0.0138 | 0.0193 | 1769 | C00762 | 02802 |
| glycolate (hydroxyacetate) | 1.04 | 0.086 | 0.0871 | 15737 | C00160 | 00115 |
| 4-hydroxyhippurate | 0.8 | 0.0114 | 0.0166 | 35527 | | |
| octanoylcarnitine | 1.03 | 0.0188 | 0.0247 | 33936 | C02838 | 00791 |
| myristate (14:0) | 1.12 | 0.0001 | 0.0004 | 1365 | C06424 | 00806 |
| 1,7-dimethylurate | 1.09 | 0.0235 | 0.03 | 34400 | C16356 | 11103 |
| 1-methylurate | 0.93 | 0.2911 | 0.2129 | 34395 | | 03099 |
| nicotinamide | 1.06 | 0.1676 | 0.147 | 594 | C00153 | 01406 |
| 1-palmitoleoylglycerophosphoethanolamine | 1.33 | 0.0119 | 0.0171 | 34565 | | |
| glycerophosphorylcholine (GPC) | 0.91 | 0.0008 | 0.0018 | 15990 | C00670 | 00086 |
| kynurenine | 1.06 | 0.0021 | 0.0041 | 15140 | C00328 | 00684 |
| 1-linoleoylglycerophosphoethanolamine | 0.94 | 0.025 | 0.0317 | 32635 | | 11507 |
| 12-HETE | 1.14 | 0.105 | 0.102 | 37536 | | 06111 |
| glycoursodeoxycholate | 0.91 | 0.3843 | 0.2476 | 39379 | | 00708 |

Example 3

Selected, Priority Biomarkers

The biomarkers for cardiometabolic disease progression, such as Type 2 diabetes (T2D), Myocardial Infarction (MI), or stroke were selected based upon the following criteria: (a) biomarkers predictive of T2D progression with a >10% fold change observed in both T2D time intervals of 3 years and 5 years and having p<0.05; (b) biomarkers predictive of T2D progression with a >15% fold change in at least one T2D time interval (3 years or 5 years) AND with statistical trending (p<0.1) in other T2D time interval (e.g. alpha-hydroxyisovalerate) OR biomarker having physiological features relevant to said disease (e.g. erythrose); (c) biomarkers predictive of T2D progression with a >20% fold change in one T2D time interval (3 years or 5 years, e.g. trehalose, n-butyl oleate); (d) other statistical measures from our metabolomics screening and targeted data indicating biomarker significance (e.g. glycerol-3-phosphate; (e) biomarkers predictive of MI or stroke with a >15% fold observed change in analyte levels compared to "progressors" of said disease versus "non-progressors". The selected priority biomarkers have p<0.05, q<0.1 and were ranked among the top 50 biomarker candidates in RF importance plots. These biomarkers are measured in plasma samples from subjects and the values obtained from the measurements are used in a mathematic model (e.g., logistic regression) to determine or aid in determining the progression of insulin resistance or pre-diabetes to the associated disorders of type 2 diabetes or cardiovascular disease (e.g., myocardial infarction or stroke) and/or the susceptibility of the subject to develop these cardiometabolic diseases.

3A. Selected Biomarkers for Development of or Progression to T2D:

The biomarkers are: 3-phenylpropionate (hydrocinnamate), 3-(4-hydroxyphenyl)lactate, indolelactate, 5-oxoproline, bradykinin-hydroxy-pro(3), mannose, 7-alpha-hydroxy-3-oxo-4-cholestenoate (7-Hoca), heme, adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate, erythrose, glycerol-3-phosphate, isoleucine, valine.

3B. Selected Biomarkers for Development of or Progression to Stroke/MI:

The biomarkers are: 3-indoxylsulfate, propionylcarnitine, 3-dehydrocarnitine, acetylcarnitine, oleoylcarnitine, myo-inositol, 5alpha-pregnan-3beta, 20alpha-diol disulfate, 5alpha-pregnan-3alpha, 20beta-diol disulfate, xanthine, trigonelline (N'-methylnicotinate), 2-hydroxyhippurate (salicylurate), piperidine, 1-methylurate, 1,3-dimethylurate, 1,7-dimethylurate, 1,3,7-54imethylurate, kynurenine.

3C. Selected Biomarkers for Development of or Progression to Cardiovascular Disease, IR/IGT, T2D:

The biomarkers are: adrenate, alpha-hydroxyisovalerate, glutamine, glycine, tyrosine, deoxycholate, cinnamoylglycine, dehydroisoandrosterone sulfate (DHEA-S), 5alpha-androstan-3beta, 17alpha-diol disulfate, urate.

Example 4

Comparison of Biomarkers and Algorithms to Current Clinical Tests for Prediction of Progression to Type-2 Diabetes, Cardiovascular Disease The performance of IR Biomarkers Model was compared with the results of the OGTT and FPG test in a cohort of 401 subjects. The IR Biomarkers Model had better Sensitivity, Specificity, Positive Predictive Value and Negative Predictive Value than either the Oral Glucose Tolerance Test (OGTT) or Fasting Plasma Glucose (FPG), two widely and currently used clinical tests. The results of the comparison of IR biomarkers with these clinical assays currently used to measure insulin resistance and type 2 diabetes are summarized in Table 6.

TABLE 6

Comparison of IR Biomarkers in instant application with Clinical
Assays currently used to measure insulin resistance and type 2 diabetes

| TEST | Sensitivity (%) | Specificity (%) | PPV (%) | NPV (%) |
|---|---|---|---|---|
| IR Biomarkers Model (AHB, LGPC, Oleate, BMI, insulin) | 62.2 | 93.8 | 83.2 | 83.3 |
| OGTT | 46.2 | 92.5 | 75.3 | 77.6 |
| FPG | 33.6 | 85.5 | 56.1 | 50.0 |

Plasma samples from a subset of the 401 subjects in the cohort that had data available for insulin, glucose disposal (Rd), adiponectin and results from the OGTT and HOMA-IR tests were evaluated for the correlation with Rd, the glucose disposal rate measurement obtained from the HI clamp. A total of 369 plasma samples from the 369 subjects where this data was available were analyzed. Subjects that had missing values were not included; 14 subjects were missing Fasting Insulin values and 2 additional subjects were missing values for adiponectin. These results and the result obtained on the same 369 subjects with the IR Model: SQRTRD~BMI+2 Hydroxybutyrate+Linoleate (x)+ Linolyl_GPC+decanoylcarnitine are shown in Table 14. The IR Model was significantly correlated (p-value=2.01E-54) with Rd and showed a better R value than did any of the other markers or models. The IR Model also had better diagnostic performance based upon the AUC, Sensitivity, Specificity, Negative Predictive Value and Positive Predictive Value than any of the other tests. In addition, the biomarkers and models provided herein demonstrate a similar correlation with glucose disposal than the HI clamp.

TABLE 7

Comparison of IR model with other commonly used tests, algorithms
and biomarkers to determine insulin sensitivity in a subject.

| Dx Test | N | R | P-value | AUC | Sens | Spec | NPV | PPV |
|---|---|---|---|---|---|---|---|---|
| IR Model | 369 | 0.71 | 2.01E−54 | 74.8 | 59.5 | 90.1 | 75.8 | 81.1 |
| OGTT | 369 | NA | NA | 68.0 | 43.7 | 92.2 | 74.3 | 75.9 |
| FPG | 369 | −0.16 | 0.002072 | 58.7 | 31.8 | 85.6 | 53.3 | 70.8 |
| HOMA-IR | 369 | −0.56 | 1.44E−31 | 70.0 | 50.8 | 89.3 | 71.1 | 77.8 |
| Adiponectin | 369 | 0.31 | 7.44E−10 | 57.6 | 35.0 | 80.3 | 47.8 | 70.4 |

The ability of the biomarkers to predict individuals who will progress to Type 2 Diabetes (T2D), Myocardial infarction (MI) or stroke was evaluated using Random Forest regression analysis to classify the subjects as "Non-Progressors" or "Progressors" based on the baseline measured values of the biomarkers and/or the measured values of the clinical parameters of sex, age, Body Mass Index (BMI), fasting plasma glucose (FPG), and fasting insulin. These clinical parameters are used currently by clinicians to evaluate the risk of a subject developing T2D, MI or stroke. The Random Forest analyses for each outcome (T2D, MI, Stroke) was carried out using 1) the clinical factors alone, 2) all of the biomarkers in Tables 1, 2, 3, 4 and 5 alone, 3) the selected subset of the biomarkers alone, or 4) the selected subset of biomarkers plus the clinical factors. The cohort is described in Example 2. The results of the analyses are presented in Tables 8, 9 and 10. In Table 8, the results of the classification of the 131 subjects that progressed to T2D and the 262 subjects that did not progress (non-progressors) are presented. In Table 9, the results of the classification of the 105 subjects that progressed to MI and the 262 subjects that did not progress (non-progressors) are presented. In Table 10, the results of the classification of the 45 subjects that progressed to stroke and the 262 subjects that did not progress (non-progressors) are presented. In each analysis, the biomarkers correctly classified the subjects as "Progressors" or "Non-progressors" with better predictive accuracy than was achieved with the clinical parameters alone. Using the selected biomarkers in combination with the clinical factors improved predictive accuracy. The diagnostic parameters of sensitivity, specificity and the prediction accuracy are presented in the Tables.

TABLE 8

T2D RF Analysis Summary

| Test | Sensitivity | Specificity | Accuracy (Error) |
|---|---|---|---|
| Clinical factors only | 63.3% | 59.7% | 61.1% (39.9) |
| All Biomarkers only | 70% | 66.3% | 66.7% (33.3) |
| Selected biomarkers | 76% | 67% | 67.9% (32.1) |
| Clinical factors + Selected biomarkers | 71.4% | 70.1% | 70.7% (29.7) |

TABLE 9

MI RF Analysis Summary

| Test. | Sensitivity | Specificity | Accuracy (Error) |
|---|---|---|---|
| Clinical factors only | 64.2% | 63% | 63.3% (36.7) |
| All Biomarkers only | 64% | 65.6% | 65.2% (34.8) |
| Selected biomarkers | 62.4% | 61.4% | 61.7% (38.3) |
| Clinical factors + Selected biomarkers | 63.4% | 65.6% | 65.1% (34.9) |

TABLE 10

RF Analysis Stroke Summary

| Test | Sensitivity | Specificity | Accuracy (Error) |
|---|---|---|---|
| Clinical factors only | 61.4% | 56.8% | 57.3% (42.7) |
| All Biomarkers only | 69% | 67.8% | 68% (32) |
| Selected biomarkers | 63.8% | 64% | 64% (36) |
| Clinical factors + Selected biomarkers | 68.4% | 65.3% | 65.6% (34.4) |

While the invention has been described in detail and with reference to specific embodiments thereof, it will be apparent to one skilled in the art that various changes and modifications can be made without departing from the spirit and scope of the invention.

What is claimed is:

1. A method for generating a risk score useful for determining the probability that a subject will progress from being normal to having one or more disorders selected from the group consisting of Insulin Resistance, Impaired Glucose Tolerance, Type-2 diabetes, and CVD, the method comprising:
producing an analytical sample by extracting small molecules from a biological sample from the subject;
determining the levels of cinnamoylglycine, 5alpha-androstan-3beta,17alpha-diol disulfate, adrenate and 3-hydroxypropanoate; and analyzing the levels of cinnamoylglycine, adrenate, 5alpha-androstan-3beta,17alpha-diol disulfate and 3-hydroxypropanoate in the sample by a statistical analysis to generate a risk score, wherein the risk score can be used to aid in determining the probability that the subject will progress to one or more disorders selected from Insulin Resistance, CVD, Type 2 diabetes, and Impaired Glucose Tolerance.

2. The method of claim 1, wherein the statistical analysis comprises a logistic regression model.

3. The method of claim 1, wherein the risk score is generated to aid in predicting the progression to cardiovascular disease.

4. The method of claim 1, further comprising:
determining the level(s) of one or more additional small molecule biomarkers in the biological sample, wherein the additional biomarkers are selected from the group consisting of 7-alpha-hydroxy-3-oxo-4-cholestenoate (7-Hoca), 3 hydroxy-2-oxovalerate, beta-hydroxypyruvate, palmitoyl sphingomyelin, oleoylcarnitine, 1-methylurate, 1,3-dimethylurate, 1,7-dimethylurate, 1,3,7-trimethylurate, and 5alpha-pregnan-3beta,20alpha-diol disulfate; and
analyzing the levels of cinnamoylglycine, adrenate, 5alpha-androstan-3beta,17alpha-diol disulfate and 3-hydroxypropanoate and the level(s) of the one or more additional biomarkers in the sample by a statistical analysis to generate a risk score, wherein the risk score can be used to aid in determining the probability that the subject will progress to one or more disorders selected from Insulin Resistance, CVD, Impaired Glucose Tolerance and Type 2 diabetes.

5. The method of claim 4, wherein the analyzing step comprises generating a probability curve using a multivariate regression model based on the measured levels of cinnamoylglycine, adrenate, 5alpha-androstan-3beta,17alpha-diol disulfate and 3-hydroxypropanoate; and level(s) of the one or more additional biomarkers.

6. The method of claim 5, wherein the probability curve is generated using a multivariate regression model based on the measured levels of cinnamoylglycine, adrenate, 7-alpha-hydroxy-3-oxo-4-cholestenoate (7-Hoca), 3-hydroxypropanoate, 3-hydroxy-2-oxovalerate, beta-hydroxypyruvate, palmitoyl sphingomyelin, oleoylcarnitine, 1-methylurate, 1,3-dimethylurate, 1,7-dimethylurate, 1,3,7-trimethylurate, 5 alpha-androstan-3beta,17alpha-diol disulfate, and 5alpha-pregnan-3beta, 20alpha-diol disulfate.

7. The method of claim 5, wherein the probability curve is generated using a multivariate regression model using the measured levels of the cinnamoylglycine, adrenate, 5alpha-androstan-3beta,17alpha-diol disulfate and 3-hydroxypropanoate and one or more additional biomarkers selected from the group consisting of 7-alpha-hydroxy-3-oxo-4-cholestenoate (7-Hoca), 3 hydroxy-2-oxovalerate, beta-hydroxypyruvate, palmitoyl sphingomyelin, oleoylcarnitine, 1-methylurate, 1,3-dimethylurate, 1,7-dimethylurate, 1,3,7-trimethylurate, and 5alpha-pregnan-3beta,20alpha-diol disulfate.

8. The method of claim 4, wherein the risk score is generated to aid in predicting the progression to Type-2 diabetes and the one or more additional biomarker comprises 7-alpha-hydroxy-3-oxo-4-cholestenoate (7-Hoca).

9. A method of generating a risk score to aid in determining susceptibility of a subject to type-2 diabetes, the method comprising:
producing an analytical sample by extracting small molecules from a biological sample from the subject;
analyzing the analytical sample from the subject to determine the levels of cinnamoylglycine, adrenate, 5alpha-androstan-3beta,17alpha-diol disulfate and 3-hydroxypropanoate; and
analyzing the levels of cinnamoylglycine, adrenate, 5alpha-androstan-3beta,17alpha-diol disulfate and 3-hydroxypropanoate by a statistical analysis to generate a risk score, wherein the risk score aids in determining whether the subject is susceptible to developing type-2 diabetes.

10. The method of claim 9, further comprising:
determining the level(s) of one or more additional small molecule biomarkers in the biological sample, wherein the additional biomarkers are selected from the group consisting of 7-alpha-hydroxy-3-oxo-4-cholestenoate (7-Hoca), 3 hydroxy-2-oxovalerate, beta-hydroxypyruvate, palmitoyl sphingomyelin, oleoylcarnitine, 1-methylurate, 1,3-dimethylurate, 1,7-dimethylurate, 1,3,7-trimethylurate, and 5alpha-pregnan-3beta, 20alpha-diol disulfate; and
analyzing the levels of cinnamoylglycine, adrenate, 5alpha-androstan-3beta,17alpha-diol disulfate and 3-hydroxypropanoate and the level(s) of the one or more additional biomarkers in the sample by a statistical analysis to generate a risk score, wherein the risk score aids in determining whether the subject is susceptible to developing type-2 diabetes.

11. The method of claim 10, wherein the one or more additional biomarkers comprise 7-alpha-hydroxy-3-oxo-4-cholestenoate (7-Hoca).

12. A method of determining susceptibility of a subject to cardiovascular disease, the method comprising:
analyzing the biological sample from the subject to determine the levels of cinnamoylglycine, adrenate, 5 alpha-androstan-3beta,17alpha-diol di sulfate and 3-hydroxypropanoate; and
comparing the levels of cinnamoylglycine, adrenate, 5alpha-androstan-3beta,17alpha-diol disulfate and 3-hydroxypropanoate to CVD-positive and/or CVD-negative reference levels thereof in order to determine whether the subject is susceptible to developing cardiovascular disease.

13. The method of claim 12, further comprising:
analyzing the biological sample from the subject to determine the levels of cinnamoylglycine, adrenate, 5alpha-androstan-3beta,17alpha-diol disulfate and 3-hydroxypropanoate and one or more additional biomarkers selected from the group consisting of 7-alpha-hydroxy-3-oxo-4-cholestenoate (7-Hoca), 3 hydroxy-2-oxovalerate, beta-hydroxypyruvate, palmitoyl sphingomyelin, oleoylcarnitine, 1-methylurate, 1,3-dimethylurate, 1,7-dimethylurate, 1,3,7-trimethylurate, and 5alpha-pregnan-3beta, 20alpha-diol disulfate; and
comparing the levels of cinnamoylglycine, adrenate, 5alpha-androstan-3beta,17alpha-diol disulfate and 3-hydroxypropanoate and the one or more additional biomarkers in the sample to CVD-positive and/or CVD-negative reference levels thereof in order to determine whether the subject is susceptible to developing cardiovascular disease.

14. The method of claim 13, wherein the cardiovascular disease is selected from the group consisting of myocardial infarction and stroke.

15. The method of claim 13, wherein the comparing step comprises generating a cardiovascular disease risk score for the subject in order to determine the susceptibility to cardiovascular disease in the subject.

16. A method of generating a risk score to aid in monitoring the progression or regression of insulin resistance in a subject, the method comprising:

producing an analytical sample by extracting small molecules from a biological sample from the subject;

analyzing the analytical sample from the subject to determine the levels of cinnamoylglycine, adrenate, 5alpha-androstan-3beta,17alpha-diol di sulfate and 3-hydroxypropanoate; and analyzing the levels of cinnamoylglycine, adrenate, 5alpha-androstan-3beta,17alpha-diol disulfate and 3-hydroxypropanoate in the sample by a statistical analysis to generate a risk score, wherein the risk score is used to aid in monitoring the progression or regression of insulin resistance in the subject.

17. The method of claim 16, further comprising:

analyzing the biological sample from the subject to determine the levels of cinnamoylglycine, adrenate, 5alpha-androstan-3beta,17alpha-diol disulfate and 3-hydroxypropanoate and one or more additional small molecule biomarkers selected from the group consisting of 7-alpha-hydroxy-3-oxo-4-cholestenoate (7-Hoca), 3 hydroxy-2-oxovalerate, beta-hydroxypyruvate, palmitoyl sphingomyelin, oleoylcarnitine, 1-methylurate, 1,3-dimethylurate, 1,7-dimethylurate, 1,3,7-trimethylurate, and 5alpha-pregnan-3beta,20alpha-diol disulfate; and analyzing the levels of cinnamoylglycine, adrenate, 5alpha-androstan-3beta,17alpha-diol disulfate and 3-hydroxypropanoate and the one or more additional biomarkers in the sample by a statistical analysis to generate a risk score, wherein the risk score is used to aid in monitoring the progression or regression of insulin resistance in the subject.

18. The method of claim 17, wherein the subject is selected from the group consisting of a subject being treated with a pharmaceutical composition, a subject having undergone bariatric surgery, a subject undergoing an exercise modification, and a subject using a dietary modification.

19. The method of claim 17, wherein the analyzing step comprises transforming the biological sample by protein extraction.

20. The method of claim 17, wherein the disease risk score is a cardiovascular disease risk score.

21. The method of claim 17, wherein the disease risk score is a type 2 diabetes risk score.

22. The method of claim 21 wherein the one or more additional biomarkers comprise 7-alpha-hydroxy-3-oxo-4-cholestenoate (7-Hoca).

* * * * *